United States Patent
Salter Venzon et al.

(10) Patent No.: US 9,737,582 B2
(45) Date of Patent: Aug. 22, 2017

(54) **METHOD FOR IMPROVING MEMORY OF A SUBJECT USING A COMPOSITION COMPRISING *CISTANCHE* AND *GINKGO* EXTRACTS**

(71) Applicant: Access Business Group International LLC, Ada, MI (US)

(72) Inventors: Dawna S. Salter Venzon, La Habra, CA (US); Mary A. Murray, Irvine, CA (US)

(73) Assignee: Access Business Group International LLC, Ada, MI (US)

( * ) Notice: Subject to any disclaimer, the term of this patent is extended or adjusted under 35 U.S.C. 154(b) by 209 days.

(21) Appl. No.: 14/707,132

(22) Filed: May 8, 2015

(65) Prior Publication Data

US 2015/0320818 A1 Nov. 12, 2015

Related U.S. Application Data

(60) Provisional application No. 61/990,200, filed on May 8, 2014, provisional application No. 62/081,104, filed on Nov. 18, 2014.

(51) Int. Cl.
*A01N 65/00* (2009.01)
*A61K 36/64* (2006.01)
*A61K 36/16* (2006.01)
*A23L 33/105* (2016.01)

(52) U.S. Cl.
CPC .......... *A61K 36/64* (2013.01); *A23L 33/105* (2016.08); *A61K 36/16* (2013.01)

(58) Field of Classification Search
CPC ................................................ A61K 36/00
USPC ..................................................... 424/725
See application file for complete search history.

(56) References Cited

U.S. PATENT DOCUMENTS 7,087,252 B2    8/2006    Tu et al.

FOREIGN PATENT DOCUMENTS

| CN | 101314001 A | 12/2008 |
|---|---|---|
| CN | 102078393 A | 6/2011 |
| CN | 102698083 A | 10/2012 |
| CN | 103125632 A | 6/2013 |
| CN | 104056042 A | 9/2014 |
| CN | 104208419 A | 12/2014 |

OTHER PUBLICATIONS

English language abstract for CN102078393A extracted from http://worldwide.espacenet.com database on Jul. 1, 2015, 1 page
English language abstract for CN102698083A extracted from http://worldwide.espacenet.com database on Jul. 1, 2015, 1 page.
English language abstract for CN103125632A extracted from http://worldwide.espacenet.com database on Jul. 1, 2015, 1 page.
English language abstract for CN104056042A extracted from http://worldwide.espacenet.com database on Jul. 1, 2015, 1 page.
English language abstract for CN104208419A extracted from http://worldwide.espacenet.com database on Jul. 1, 2015, 1 page.
Geng X, Song L, Pu X, Pengfei T. (2004). Neuroprotective effects of phenylethanoid glycosides from Cistanches against 1-methyl-4-phenyl-1,2,3,6-tetrahydropyridine (MPTP) induced dopaminergic toxicity in C57 mice. Biol Pharm Bull 27:797-801.
Kuang RM, Sun Y, Yuan W, et al. (2009). Protective effects of echinacoside, one of the phenylethanoid glycosides, on the H2O2-induced cytotoxicity in PCI2 cells. Plant Med.75:1499-1504.
Zhao Q, Gao J, Li W. (2010). Neurotrophic and neurorescue effects of Echinacoside in the subacute MPTP mouse model of Parkinson's disease. Brain Research. 1346:224-236.
Choi JG, Moon M, Jeong Hu, Kim MC, et al. (2011). Cistanches herba enhances learning and memory by inducing nerve growth factor. Behav Brain Res. 216:652-658.
Memory Builder with Ginko Dietary Supplement product label. www.nutrilite.com, 1026913, Jan. 31, 2011.
English language abstract and machine assisted translation for CN101314001A extracted from http://worldwide.espacenet.com database on Aug. 13, 2015 and Aug. 25, 2015, 20 pages.
David E. Hartley et al., "Effects on cognition and mood in post-menopausal women of 1-week treatment with Ginko biloba", Pharmacology Biochemistry and Behavior, vol. 75, No. 3, Jun. 1, 2003, pp. 711-720.
J G Choi et al., "Cistanches Herba enhances learning and memory by inducing nerve growth factor", Behavioural Brain Research, Elsevier, Amsterdam, NL, vol. 216, No. 2, Jan. 20, 2011, pp. 652-658.
Anonymous: "Nutrilite Memory Builder Dietary Supplement", Dec. 13, 2011, XP055200775, http://www.amazon.com Retrieved from the Internet: URL :http://www.amazon.com/Nutrilite-Memory-Builder-Dietary-Supplement/dp, retrieved on Jul. 7, 2015, 4 pages.
PCT/US2015/029819 International Search Report dated Jul. 31, 2015, 4 pages.

*Primary Examiner* — Michael Meller
(74) *Attorney, Agent, or Firm* — Warner Norcross & Judd LLP

(57) ABSTRACT

A method and composition useful for improving memory of a subject are disclosed. The method comprises the step of administering the composition to the subject. The composition consists essentially of *Cistanche* extract and *Ginkgo* extract (e.g. as actives). In a first general embodiment, the extracts are present in a weight ratio (*Cistanche* to *Ginkgo*; or "C:G") that is >2.5:1. In a second general embodiment, the extracts are present in a weight ratio that is <2.5:1. In embodiments of the first general embodiment, the composition comprises about 72-99 weight percent (wt. %) *Cistanche tubulosa* extract and about 1-28 wt. % *Ginkgo biloba* extract. In embodiments of the second general embodiment, the composition comprises about 50-70 wt. % *Cistanche tubulosa* extract and about 30-50 wt. % *Ginkgo biloba* extract. The *Cistanche tubulosa* extract is generally obtained from root material and the *Ginkgo biloba* extract is generally obtained from leaf material. The composition may also include inactives.

9 Claims, 27 Drawing Sheets

Neuron/Glia Co-Cultures on Micro-Electrode Array Chips

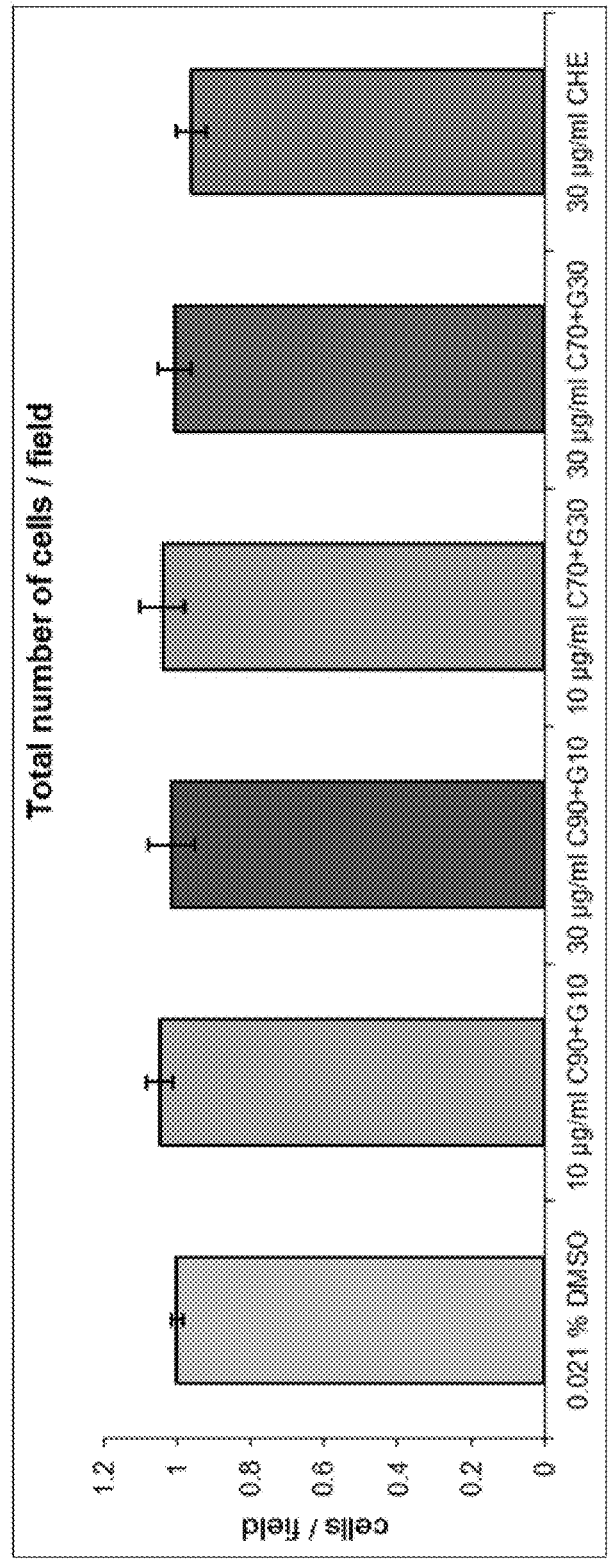

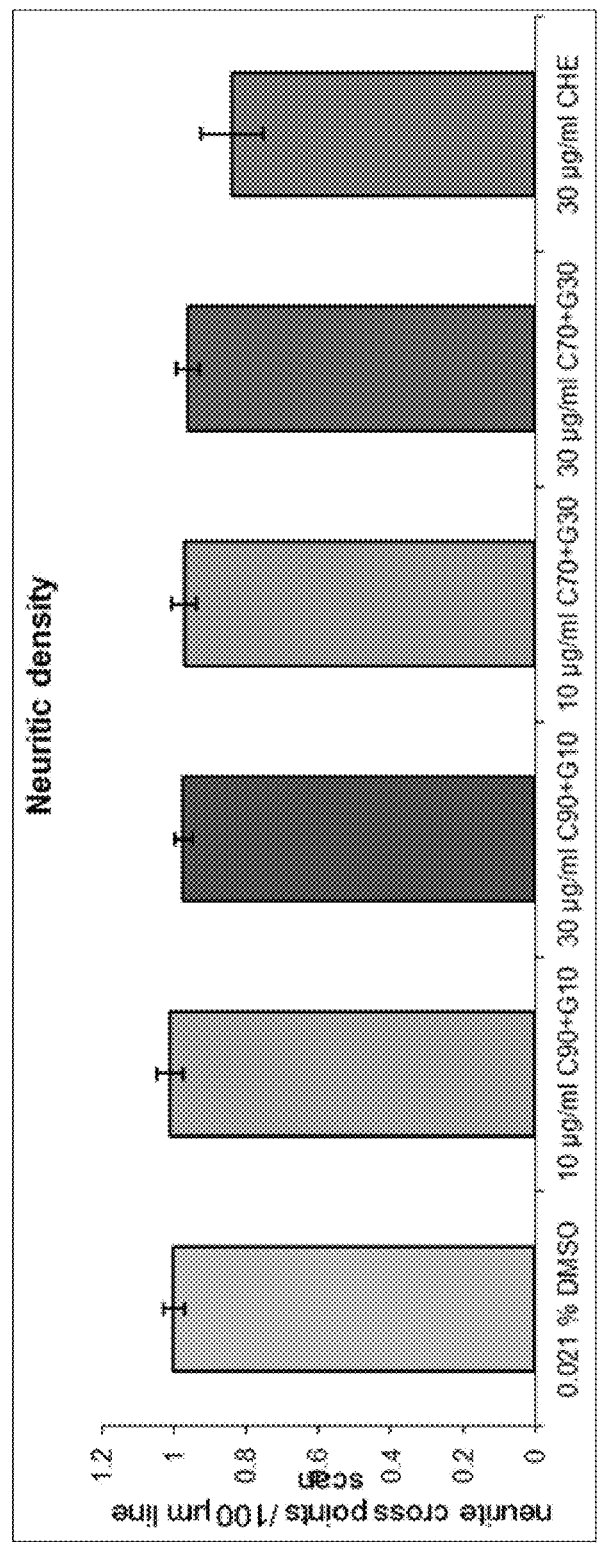

METHOD FOR IMPROVING MEMORY OF A SUBJECT USING A COMPOSITION COMPRISING *CISTANCHE* AND *GINKGO* EXTRACTS

CROSS-REFERENCE TO RELATED APPLICATIONS

This application claims priority to and all advantages of U.S. Pat. App. No. 61/990,200 filed on May 8, 2014 and U.S. Pat. App. No. 62/081,104 filed on Nov. 18, 2014, the content of which is hereby incorporated by reference

FIELD OF THE INVENTION

The present invention generally relates to a method and composition for improving memory of a subject. The method comprises the step of administering the composition to the subject. The composition consists essentially of *Cistanche* and *Ginkgo* extracts.

DESCRIPTION OF THE RELATED ART

Short-term memory is supported by transient patterns of neuronal communication, dependent on regions of the frontal and parietal lobes. On the other hand, long-term memory is maintained by more stable and permanent changes in neural connections widely spread throughout the brain. It is believed that the hippocampus is essential to the consolidation of information from short- to long-term memory, although it does not seem to store information itself.

A number of efforts have been made to improve short- and long-term memories. For example, dietary supplements have been provided in an effort to improve brain health and mental performance. A specific example of such is the "Memory Builder™ with *Ginkgo*" dietary supplement from NUTRILITE® of Buena Park, Calif., US. This dietary supplement is in the form of a tablet consisting of the following active ingredients: 300 mg *Cistanche tubulosa* extract (root) and 120 mg *Ginkgo biloba* extract (leaves).

While various efforts have been made, there remains an opportunity to provide additional methods and compositions for improving brain health, memory formation, and/or memory retention. Moreover, there remains an opportunity to reverse, slow, or prevent memory loss.

BRIEF SUMMARY OF THE INVENTION

A method and a composition are disclosed. The method and composition are useful for improving memory of a subject. The method comprises the step of administering the composition to the subject. The composition consists essentially of *Cistanche* extract and *Ginkgo* extract. In a first general embodiment, the extracts are present in a weight ratio (*Cistanche* to *Ginkgo*; or "C:G") that is >2.5:1. In a second general embodiment, the extracts are present in a weight ratio (C:G) that is <2.5:1.

In various embodiments of the first general embodiment of this disclosure, the composition comprises about 72-99 weight percent (wt. %) *Cistanche tubulosa* extract and about 1-28 wt. % *Ginkgo biloba* extract. In these embodiments, the *Cistanche tubulosa* and *Ginkgo biloba* extracts are present in a weight ratio (C:G) that is from 2.6:1 to 20:1. In various embodiments of the second general embodiment of this disclosure, the composition comprises about 50-70 wt. % *Cistanche tubulosa* extract and about 30-50 wt. % *Ginkgo biloba* extract. In these embodiments, the *Cistanche tubulosa* and *Ginkgo biloba* extracts are present in a weight ratio (C:G) that is from 1:1 to 2.4:1. The *Cistanche tubulosa* extract is generally obtained from root material and the *Ginkgo biloba* extract is generally obtained from leaf material.

Without being bound or limited by any particular theory, it is thought that the method and composition of this disclosure are useful for improving brain health, memory formation, and/or memory retention. Moreover, it is thought that the method and composition of this disclosure are useful for reversing, slowing, or preventing memory loss.

BRIEF DESCRIPTION OF THE DRAWINGS

Other advantages of the disclosure will be readily appreciated, as the same becomes better understood by reference to the following detailed description when considered in connection with the accompanying drawings wherein:

FIG. 20A is a bar chart illustrating chronic application effects on hippocampal network morphology of examples;

FIG. 20C is a bar chart illustrating chronic application effects on hippocampal network morphology of examples;

DETAILED DESCRIPTION OF THE INVENTION

Figure 1A:
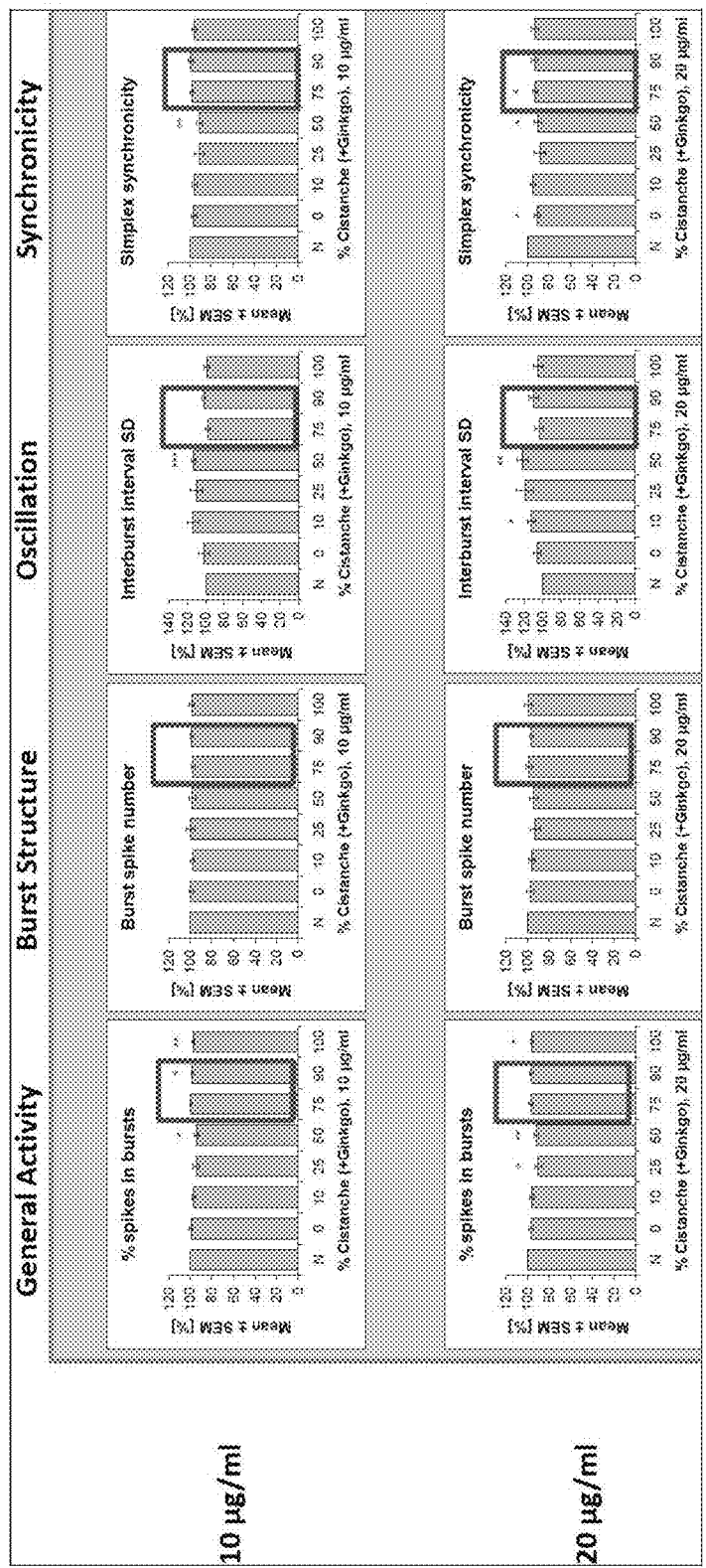
FIG. 1A depicts bar charts of acute application examples.

A method and a composition are disclosed. The method and composition are useful for improving memory of a subject. The method comprises the step of administering the composition to the subject. Without being bound or limited by any particular theory, it is thought that the method and composition of this disclosure are useful for improving brain health, memory formation, and/or memory retention. Moreover, it is thought that the method and composition of this disclosure are useful for reversing, slowing, or preventing memory loss. Other potential non-limiting benefits are described herein.

The composition consists essentially of *Cistanche* extract and *Ginkgo* extract. As used herein, the phrase "consisting essentially of" generally encompasses the specifically recited elements/components for a particular embodiment. Further, the phrase "consisting essentially of" generally encompasses and allows for the presence of additional or optional elements/components that do not materially impact the basic and/or novel characteristics of that particular embodiment. In certain embodiments, "consisting essentially of" allows for the presence of ≤10, ≤5, or ≤1, weight percent (wt. %) of additional or optional components based on the total weight of the composition. In other embodiments, the composition consists of *Cistanche* extract and *Ginkgo* extract as described herein. The aforementioned extracts may be referred to herein as the extracts, actives, or active ingredients. In various embodiments, actives of the composition consist of the *Cistanche* (or "*Herba Cistanche*") and *Ginkgo* (or "Yin Xing Ye") extracts.

Components that would generally materially impact the method/composition of this disclosure include active ingredients that are different from *Cistanche* extract and *Ginkgo* extract. In certain embodiments, the composition of this disclosure is free of other active ingredients. By "other active ingredients", it is generally meant that the composition is free of other types of Traditional Chinese Medicines ("TCMs"; or "Chinese medicines") that are different from *Cistanche* extract and *Ginkgo* extract. Other types of TCMs are understood in the art. Examples of other types of TCMs are generally described as "bioactive substances" in International Pub. No. WO01/22934A2, the content of which is incorporated by reference in its entirety.

In certain embodiments, the composition of this disclosure can comprise inactive ingredients as described below. If utilized, the inactive ingredients are different from *Cistanche*, *Ginkgo*, and other active ingredients.

Components that would not generally impact the method/composition of this disclosure include inactive ingredients. Inactive ingredients are understood in the art and are different from active ingredients, such as those described above. Examples of inactive ingredients include, but are not limited to, flavorings; carob; corn syrups, such as hydrolyzed corn syrup solids; cellulose, such as methyl cellulose, hydroxypropyl methyl cellulose, carboxy methyl cellulose, microcrystalline cellulose, and powdered cellulose; fructose; maltodextrin and maltol, such as natural maltol; sorbitol; preservatives; alcohols, such as ethanol, propyl alcohol and benzyl alcohol; glycerin; potassium sorbate; sodium benzoate; binders; flow agents; stearates, such as calcium stearate, magnesium stearate, and sodium magnesium stearate; dicalcium phosphate; glyceryl triacetate; vegetable oils, such as hydrogenated vegetable oils; mineral oils; water; silicones, such as silicone oils; silicon dioxide; stearic acid; waxes, such as carnauba wax and beeswax; starches, such as corn starch and potato starch; fatty esters and fatty alcohols; glycols and polyglycols; and combinations thereof. If utilized to form the composition, the inactive ingredient(s) can be used in various amounts. Further, it is to be appreciated that the amounts of actives described herein can be normalized with respect to 100 parts by weight of the composition to account for the presence of inactive ingredients (if utilized). This disclosure is not limited to a particular inactive ingredient or amount thereof.

The composition includes *Cistanche* extract. The *Cistanche* extract is obtained from plant material from the genus *Cistanche*. *Cistanche* is a worldwide genus of holoparasitic desert plants in the order Lamiales, family Orobanchaceae. Notable species of this genus include *Cistanche (C.) ambigua, C. deserticola, C. phelypaea, C. salsa, C. sinensis*, and *C. tubulosa*. These species can be found in the arid lands of China and Pakistan and other parts of the world. In certain embodiments, *C. deserticola* is not utilized based on scarcity.

In many embodiments, the *Cistanche* extract is an extract from the species *Cistanche tubulosa* (Shrenk.) Wight (also known simply as *Cistanche tubulosa*). *Cistanche* (root) may also be referred to as "*Herba Cistanche*" according to the Chinese Pharmacopeia. *Herba Cistanche* may also be referred to as Rou Cong Rong, 苁蓉, 肉苁蓉, 大芸, Desertliving *Cistanche*, Cong Rong, 肉苁蓉, 苁蓉, or 大蕓.

As used herein, reference to "*Cistanche* extract" generally refers to an extract containing material from the genus *Cistanche* including from the species *Cistanche tubulosa*. Optionally, other *Cistanche* species may be used in addition or alternate to *Cistanche tubulosa*; however, inclusion of *Cistanche tubulosa* extract is generally preferred. The *Cistanche* extract may be commercially obtained from various resources. In addition, suitable *Cistanche* extracts can be obtained by using any conventional extraction technique including, but not limited to, one or more techniques described further below.

Any part of the *Cistanche* plant may be used to obtain the extract used in the composition including, but not limited to, the root, stem, rhizome, leaf, flower, fruit, and/or extracts of these parts. *Cistanche* actives are generally found in the root of *Cistanche* plants and as such, root extraction (or root extract) is generally most useful for purposes of this disclosure. The *Cistanche* may be used in raw form, suspended form, dehydrated form, concentrated form, or extract form. In specific embodiments, the *Cistanche* extract is obtained from root material of a plant in the genus *Cistanche*, e.g. from root material of one or more *Cistanche tubulosa* plants.

Extracts of *Cistanche* roots may contain various actives (or phytochemicals), such as phenylethanoid glycosides. Without being bound or limited by any particular theory, it is thought that active components of *Cistanche* have positive effects on neuronal health, specifically as an anti-oxidant neuroprotective and as an endothelium-dependent relaxant to help promote optimal blood flow to the brain. Further, the mechanisms by which *Cistanche* supports neuronal strength are posited to be via increasing neuronal growth factors and inhibiting neurotransmitter breakdown.

In various embodiments, the *Cistanche* extract comprises at least one phenylethanoid glycoside, or mixtures thereof, in an amount of at least about 10, at least about 20, at least about 30, at least about 40, at least about 50, at least about 60, or at least about 70, %. Moreover, the *Cistanche* extract comprises at least one acteoside, cistanoside, echinacoside, or isoacteoside, or mixtures thereof, in an amount of at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, or at least about 40, %. In all of these embodiments, an upper boundary is 100%. It is contemplated that any and all values or ranges of values between those described above may also be utilized.

The composition also includes *Ginkgo* extract (which may also be referred to as "Gingko extract" or "maidenhair tree" extract). The *Ginkgo* extract is obtained from plant (or tree) material from the genus *Ginkgo*. *Ginkgo* is a worldwide genus of plants in the order Ginkgoales, family Ginkgoaceae. Notable species of this genus include *Ginkgo* (*G.*) *aditantoides*, *G. apodes*, *G. biloba*, *G. cranei*, *G. digitata*, *G. dissecta*, *G. gardneri*, *G. ginkgoidea*, *G. huolinhensis*, *G. huttonii*, and *G. yimaensis*. These species can be found in China and other parts of the world.

In many embodiments, the *Ginkgo* extract is an extract from the species *Ginkgo biloba*. *Ginkgo* (leaf) may also be referred to as "Yin Xing Ye" according to the Chinese Pharmacopeia. Yin Xing Ye is also referred to as 银杏叶, *Ginkgo* Leaf, 白果叶, 銀杏葉, 白果葉, or Folium *Ginkgo*. *Ginkgo* (nut) may also be referred to as Bai Guo, although Yin Xing Ye is generally preferred over Bai Guo.

As used herein, reference to "*Ginkgo* extract" generally refers to an extract containing material from the genus *Ginkgo* including from the species *Ginkgo biloba*. Optionally, other *Ginkgo* species may be used in addition or alternate to *Ginkgo biloba*; however, inclusion of *Ginkgo biloba* extract is generally preferred. The *Ginkgo* extract may be commercially obtained from various resources. In addition, suitable *Ginkgo* extracts can be obtained by using any conventional extraction technique including, but not limited to, one or more techniques described further below.

Any part of the *Ginkgo* plant may be used to obtain the extract used in the composition including, but not limited to, the root, stem, rhizome, leaf, flower, fruit, and/or extracts of these parts. *Ginkgo* actives are generally found in the leaves of *Ginkgo* plants and as such, leaf extraction (or leaf extract) is generally most useful for purposes of this disclosure. The *Ginkgo* may be used in raw form, suspended form, dehydrated form, concentrated form, or extract form. In specific embodiments, the *Ginkgo* extract is obtained from leaf material of a plant in the genus *Ginkgo*, e.g. from leaf material of one or more *Ginkgo biloba* plants (i.e., *Ginkgo biloba* L.).

Extracts of *Ginkgo* leaves may contain various actives (or phytochemicals), such as flavonoid glycosides (e.g. myricetin and quercetin) and terpenoids (e.g. ginkgolides and bilobalides). *Ginkgo* plant material may also contain terpene trilactones (e.g. ginkgolides A, B, C, J and bilobalide), flavonol glycosides, biflavones, proanthocyanidins, alkylphenols, simple phenolic acids, 6-hydroxykynurenic acid, 4-O-methylpyridoxine, and polyprenols. Without being bound or limited by any particular theory, it is thought that active components of *Ginkgo* improve blood flow to the brain and act as antioxidants. Further, it is thought that memory and cognitive speed may also be improved.

In various embodiments, the *Ginkgo* extract comprises at least one flavonoid, or mixtures thereof, in an amount of at least about 1, at least about 5, at least about 10, at least about 15, at least about 20, at least about 22, at least about 24, at least about 25, at least about 30, at least about 35, or at least about 40, %. Moreover, the *Ginkgo* extract comprises at least one terpenoid, or mixtures thereof, in an amount of at least about 0.1, at least about 0.5, at least about 1, at least about 2, at least about 3, at least about 4, at least about 5, at least about 6, at least about 7, at least about 8, at least about 9, at least about 10, at least about 15, or at least about 20, %. In all of these embodiments, an upper boundary is 100%. It is contemplated that any and all values or ranges of values between those described above may also be utilized.

In a first general embodiment of this disclosure ("first embodiment"), the extracts are present in a weight ratio (*Cistanche* to *Ginkgo*; or "C:G") that is >2.5:1. In other words, the *Cistanche* extract is present in an amount more than 2.5 times that of the *Ginkgo* extract. Typically, the weight ratio is from 2.6:1 to 20:1, 2.8:1 to 15:1, 3:1 to 9:1, 3:1 to 8:1, 3:1 to 7:1, 3:1 to 6:1, 3:1 to 5:1, 3:1 to 4:1, or 3:1. Alternatively, the weight ratio is from 2.6:1 to 20:1, 2.8:1 to 15:1, 3:1 to 9:1, 4:1 to 9:1, 5:1 to 9:1, 6:1 to 9:1, 7:1 to 9:1, 8:1 to 9:1, or 9:1. It is contemplated that any and all values or ranges of values between those described above may also be utilized.

In various embodiments of the first embodiment, the *Cistanche* extract is present in an amount of from about 72-99, about 73-98, about 74-97, about 75-96, about 75-95, or about 75-90, wt. % based on 100 parts by weight of the composition. In specific embodiments, the *Cistanche* extract is present in an amount of from about 72-99, about 75-98, about 80-97, about 85-96, about 90-95, or about 90, wt. % based on 100 parts by weight of the composition. In other specific embodiments, the *Cistanche* extract is present in an amount of from about 72-99, about 73-95, about 74-90, about 75-85, about 75-80, or about 75, wt. % based on 100 parts by weight of the composition. It is contemplated that any and all values or ranges of values between those described above may also be utilized.

Moreover, the *Ginkgo* extract is present in an amount of from about 1-28, about 2-27, about 3-28, about 4-27, about 5-26, about 6-25, about 7-25, about 8-25, about 9-25, or about 10-25, wt. % based on 100 parts by weight of the composition. In specific embodiments, the *Ginkgo* extract is present in an amount of from about 1-28, about 2-25, about 3-20, about 4-15, about 5-10, or about 10, wt. % based on 100 parts by weight of the composition. In other specific embodiments, the *Ginkgo* extract is present in an amount of from about 1-28, about 5-27, about 10-26, about 15-25, about 20-25, or about 25, wt. % based on 100 parts by weight of the composition. It is contemplated that any and all values or ranges of values between those described above may also be utilized.

In certain embodiments of the first embodiment, the composition comprises about 72-99 wt. % *Cistanche tubulosa* extract and about 1-28 wt. % *Ginkgo biloba* extract. The *Cistanche tubulosa* and *Ginkgo biloba* extracts are present in a weight ratio (C:G) that is from 2.6:1 to 20:1. Moreover, the *Cistanche tubulosa* extract is obtained from root material and the *Ginkgo biloba* extract is obtained from leaf material. In specific embodiments, the *Cistanche tubulosa* extract is present in an amount of about 90 wt. % and the *Ginkgo biloba* extract is present in an amount of about 10 wt. %, each based on 100 parts by weight of the composition. In other specific embodiments, the *Cistanche tubulosa* extract is present in an amount of about 75 wt. % and the *Ginkgo biloba* extract is present in an amount of about 25 wt. %, each based on 100 parts by weight of the composition. It is contemplated that any and all values or ranges of values between those described above may also be utilized.

In a second general embodiment of this disclosure ("second embodiment"), the extracts are present in a weight ratio (C:G) that is <2.5:1. In other words, the *Cistanche* extract is present in an amount less than 2.5 times that of the *Ginkgo* extract. Typically, the *Cistanche* extract is present in an amount equal to or greater than, more typically greater than, that of the *Ginkgo* extract. Typically, the weight ratio is from 1:1 to 2.4:1, 3:2 to 7:3, 2:1 to 7:3, 2.1:1 to 7:3, 2.2:1 to 7:3; 2.3:1 to 7:3; or 7:3. It is contemplated that any and all values or ranges of values between those described above may also be utilized.

In various embodiments of the second embodiment, the *Cistanche* extract is present in an amount of from about 50-70, about 55-70, about 60-70, about 65-70, or about 70, wt. % based on 100 parts by weight of the composition. It is contemplated that any and all values or ranges of values between those described above may also be utilized.

Moreover, the *Ginkgo* extract is present in an amount of from about 30-50, about 30-45, about 30-40, about 30-40, about 30-35, or about 30, wt. % based on 100 parts by weight of the composition. It is contemplated that any and all values or ranges of values between those described above may also be utilized.

In certain embodiments of the second embodiment, the composition comprises about 50-70 wt. % *Cistanche tubulosa* extract and about 30-50 wt. % *Ginkgo biloba* extract. The *Cistanche tubulosa* and *Ginkgo biloba* extracts are present in a weight ratio (C:G) that is from 1:1 to 2.4:1. Moreover, the *Cistanche tubulosa* extract is obtained from root material and the *Ginkgo biloba* extract is obtained from leaf material. In specific embodiments, the *Cistanche tubulosa* extract is present in an amount of about 70 wt. % and the *Ginkgo biloba* extract is present in an amount of about 30 wt. %, each based on 100 parts by weight of the composition. It is contemplated that any and all values or ranges of values between those described above may also be utilized.

In various embodiments, the *Cistanche* extract is present in an amount of at least about 1, at least about 5, at least about 10, at least about 15, at least about 20, at least about 25, at least about 50, at least about 100, at least about 150, at least about 200, at least about 250, at least about 300, at least about 350, at least about 400, at least about 450, or at least about 500, mg based on the total weight of the composition. In these embodiments, an upper boundary is generally ≤5,000, ≤4,000, ≤3,000, ≤2,500, ≤2,000, ≤1,500, ≤1,000, ≤750, or ≤500, mg of *Cistanche* extract based on the total weight of the composition. It is contemplated that any and all values or ranges of values between those described above may also be utilized.

Surprisingly, it was discovered that a greater amount of *Cistanche* extract relative to *Ginkgo* extract provides synergistic benefits. Specifically, it was discovered that the extract combinations/mixtures described herein provide beneficial effects on neuronal cell signaling. Moreover, it was discovered, unexpectedly, that an excess of *Ginkgo* extract relative to *Cistanche* extract (e.g. 50% or greater) can actually have deleterious effects, specifically, by acting as an inhibitor of desired neuronal cell signaling. Other findings are described in the EXAMPLES section below.

The extracts can be obtained via conventional extraction methods understood in the art, such as by water (e.g. steam) extraction or by solvent (e.g. alcohol) extraction. The composition of this disclosure is not limited to a particular extraction method, nor is extraction required since suitable extracts (e.g. standardized extracts) are readily available from a number of commercial suppliers, such as from Sinphar Tian-Li Pharmaceutical, of Hongzhou, China and from Beijing Gingko group of Beijing, China. Exemplarily extraction methods are described below.

In order to obtain an extract, a polar solvent such as an alcohol (e.g. methanol, ethanol, butylene glycol), an ether (e.g. ethyl ether), a ketone (e.g. acetone), an ester (e.g. ethyl acetate), water, or mixtures thereof, can be used as a solvent. Certain extracts can be also obtained by further extracting the extract from the polar solvent with a non-polar solvent. Suitable non-polar solvents include, but are not limited to, ethyl acetate, hexane, dichloromethane, chloroform, or mixtures thereof.

There are a variety of extraction methods that may be used to produce extracts suitable for the composition. These methods include, but are not limited to, the extraction methods disclosed in U.S. Pat. No. 7,897,184, which is hereby incorporated by reference in its entirety and partially reproduced below with respect to some extraction methods. While extraction solvents described specifically mention ethanol, it should be understood that other alcohols such as, but not limited to, isopropyl alcohol, ethyl alcohol, and/or methyl alcohol may be used in addition to or as an alternative to ethanol. Exemplary alcoholic solvents include, but are not limited to, $C_1$-$C_4$ alcohols, such as methanol, ethanol, propanol, isopropanol, and butanol; hydro-alcohols or mixtures of alcohol and water, including hydro-ethanol; polyhydric alcohols, such as propylene glycol and butylene glycol; and fatty alcohols. Any of these alcoholic solvents may be used. Other solvents such as, but not limited to, acetone may also be used as an extraction solvent. Solvent-water blends, e.g. alcohol-water and/or acetone-water blends, of any ratio, may also be used.

In one example, the extracts can be obtained using an organic solvent extraction technique. In another example, solvent sequential fractionation can be used to obtain the extracts. Total hydro-ethanolic extraction techniques can also be used to obtain the extracts. Generally, this is referred to as a lump-sum extraction. Extracts generated in the process will contain a broad variety of phytochemicals present in the extracted material including fat and water soluble phytochemicals. Following collection of the extract solution, the solvent will be evaporated, resulting in the extract.

Total ethanol extraction may also be used. This technique uses ethanol as the solvent. This extraction technique generates an extract that may include fat soluble and/or lipophilic compounds in addition to water soluble compounds. Total methanol extraction may also be used in a similar manner with similar results.

Another example of an extraction technique that can be used to obtain the extracts is supercritical carbon dioxide supercritical fluid extraction ("SFE"). In this extraction procedure, the material to be extracted is not exposed to any organic solvents. Rather, the extraction solvent is carbon dioxide ($CO_2$), with or without a modifier, in super-critical conditions (e.g. >31.3° C. and >73.8 bar). Those of skill in the art will appreciate that temperature and pressure conditions can be varied to obtain the best yield of extract. This technique generates an extract of fat soluble and/or lipophilic compounds, similar to total hexane and ethyl acetate extraction techniques, which may also be used.

The composition can be prepared using various methods understood in the art. For example, actives of the composition, and optionally one or more inactives, can be mixed or blended and compressed or compounded utilizing various techniques understood in the art. The composition of this disclosure is not limited to a particular order of manufacturing steps or method of manufacture.

Typically, the composition is administered (or ingested) orally, e.g. via the mouth (or "per os"). More typically, at least a portion of the composition is administered (or digested) enternally, e.g. via the gastrointestinal (GI) track (or "enteros"). The subject is typically a human, and can include men and women of various ages. The method/composition of this disclosure is not limited to a particular subject.

The composition can be in various forms. Examples of suitable forms include solids, gels and liquids. Typically, the composition is solid. For example, the composition can be in the form of a pill, including tablets, capsules, and caplets. In general, each of these terms can be used interchangeably in the art, e.g. tablet for pill or vice versa. Other than the *Cistanche* and *Ginkgo* extracts (i.e., the "actives" or "active ingredients"), the composition can include inactives (or "inactive ingredients") including, but not limited to, excipients, such as diluents and binders; granulating agents; glidants (or flow aids); fillers; lubricants; preservatives; stabilizers; coatings; disintegrants; sweeteners or flavors; and pigments. Further examples of inactive ingredients are described above. In general, a number and quantity of excipients should be kept at a minimum as long as active ingredients are properly delivered. This is because subjects/consumers tend to prefer smaller tablets for easier consumption.

The composition can be in powder form, or pressed or compacted from a powder into a solid dose. A coating, e.g. polymer coating, may be used to make the tablet smoother and easier to swallow, to control release rate of the actives, to increase resiliency (or shelf life), and/or to enhance appearance. Other suitable oral forms of the composition include syrups, elixirs, suspensions, and emulsions. Further non-limiting embodiments of the composition of this disclosure are described hereafter.

In general, tablets provide a solid dosage form of delivery by oral route. Typically, the main purpose of a tablet formulation is to deliver active ingredients to a subject/consumer. Inactive ingredients are inactive substances that are generally used as carriers and formulation support for delivery of active ingredients. Inactive ingredients can be used for a variety of reasons, including handling small quantities (low mg and mcg doses) of active ingredients, accurate dosing, stabilizing unstable active ingredients, degradation of active ingredients in the stomach, diluting active ingredients to prevent potential GI tract injury, and/or masking unpleasant organoleptic properties (taste and smell) of active ingredients.

Active ingredients must become biologically available to the subject/consumer. For this purpose, active ingredients must first be dissolved and released into the body. For in vitro dissolution, the US Pharmacopeia ("USP") uses the following terms for determination of in vitro dissolution profile of dosage forms: immediate release, extended release and delayed release.

The in vivo release profile of active ingredients may be a conventional (unmodified) release, or a controlled release/sustained release (CR/SR), time release, targeted release or extended release. For CR/SR, zero-order kinetics is the ideal release profile. CR/SR profile may generally be achieved in two ways: (1) matrix, where active ingredients are dispersed within a polymer (Example: 71G NF Carbopol® polymer, Lubrizol Advanced Material Inc.) or (2) reservoir, where active and inactive ingredients form the core, which is encapsulated by membrane(s). Sometimes, a combination of different mechanisms is used (for example: CDT® controlled delivery technology, from SCOLR Pharma, which uses matrix erosion, changes in gel thickness, electrolyte ionization, and ionic interactions mechanisms).

The in vivo release can also be enhanced for bioavailability. Several factors can influence the bioavailability of active ingredients, including release rate from the delivery system, active ingredient degradation in the GI tract and poor permeability across gut mucosa. Some natural compounds have been shown to enhance the bioavailability of a number of dietary ingredients in clinical trials, for example, BioPerine® from Sabinsa.

The composition can be administered in various amounts. In certain embodiments, the composition is administered in an amount to provide at least about 1, at least about 5, at least about 10, at least about 15, at least about 20, at least about 25, at least about 50, at least about 100, at least about 150, at least about 200, at least about 250, at least about 300, at least about 350, at least about 400, at least about 450, or at least about 500, mg of the *Cistanche* extract to the subject. In these embodiments, an upper boundary of administration is generally ≤5,000, ≤4,000, ≤3,000, ≤2,500, ≤2,000, ≤1,500, ≤1,000, ≤750, or ≤500, mg of *Cistanche* extract to the subject. It is contemplated that any and all values or ranges of values between those described above may also be utilized.

The composition may be administered as needed, daily, several times per day or in any suitable regimen such that the desired outcome is achieved. In the method of this disclosure, the frequency of administration (e.g. of ingestion and/or digestion) can depend on several factors, including the desired level of memory improvement. Generally, a regimen includes administration of the composition once or twice daily to include an administration in the morning and/or an administration in the evening. The amount of composition administered may depend on several factors, including level of desired results and the specific composition.

The composition can be used for improving memory of a subject. In various embodiments, the composition is administered to the subject on a periodic basis, alternatively a daily basis, as part of a nutritional supplement regime for improving memory of the subject. In these embodiments, one or more tablets of the composition, for example, may be taken per day. Typically, ingestion of the composition (e.g. in tablet form) coincides with a meal. Without being bound or limited by any particular theory, it is thought that ingestion of *Ginkgo* (*biloba*) provides quick support for mental performance, generally 4-6 hours after taking, while *Cistanche* (*tubulosa*) can improve memory, focus and/or recall over a longer period of time, or a period of weeks, after taking.

The following examples, illustrating the compositions and methods of this disclosure, are intended to illustrate and not to limit the invention. The *Cistanche* extract may simply be indicated as "C", "CHE", or "CT" in various examples or Figures. Moreover, the *Ginkgo* extract may simply be indicated as "G" or "GB" in various examples or Figures.

EXAMPLES

A number of compositions representative of this disclosure are formulated and analyzed. Moreover, a number of comparative compounds are analyzed and compared against the aforementioned compositions. Various findings/results and testing methodologies are generally illustrated in the drawings, which are described in greater detail below.

Microelectrode array (MEA) neurochips were utilized to analyze various examples. Specifically, use of MEA neurochips enabled stimulation and recording of bioelectricity with high spatial and temporal resolution, to glean neuroactivity of the *Cistanche* and *Ginkgo* extracts, alone and in combination, and with neuronal growth factors.

MEA neurochips are available from NeuroProof GmbH of Rostock, Germany. The electrophysiological properties of compounds can be evaluated using their ability for induction of activity changes in neuronal networks grown on MEA neurochips. Routine monitoring of internal dynamics of mammalian neuronal networks is possible. The growth of neuronal networks on high-density MEA neurochips yields a hybrid test platform that allows the continuous and simultaneous monitoring of spike activity from a large number of cells for weeks or even months. The advantage of extracellular MEA-neurochip recording is the possibility of long-term recording from multiple sites in vitro and the monitoring of signal transmission between several hundred cells. Therefore, MEA neurochips enable a real time analysis of action potential patterns at both the single cell and the whole network level while providing optical access for the observation of network architecture and growth.

Data from two major areas of experimentation show: 1) ACUTE application of *Ginkgo* and *Cistanche* extracts together at specific ratios exhibit synergistic effects on neuronal cell signaling; and 2) CHRONIC treatment of *Cistanche* altered neuronal responses to Neuron Growth Factor ("NGF") over NGF alone.

Results: Acute Application

FIG. 1A depicts acute application examples, specifically bar charts from an isobolographic analysis of *Ginkgo*, *Cistanche*, and five mixtures thereof. It was found that a higher proportion of *Ginkgo* in the mixture increased the potency of the inhibitory action shown by effects at a lower total concentration of the mixture (e.g. 20-50 µg/ml).

Figure 1B:
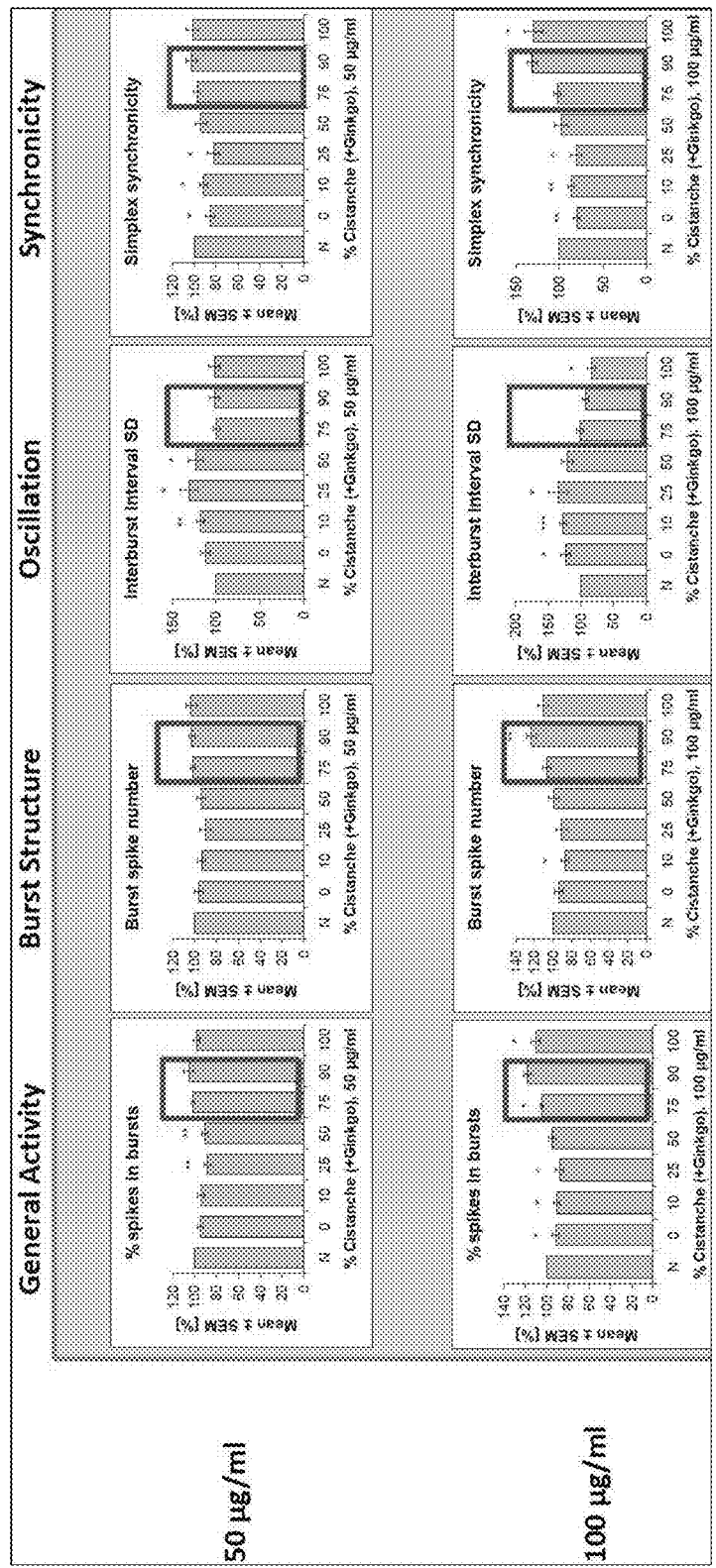
FIG. 1B depicts bar charts of further acute application examples.

FIG. 1B further depicts acute application examples, specifically bar charts showing that a higher proportion of *Cistanche* in a mixture resulted in a higher effect size. First activity enhancing effects were observed for mixtures containing 100%, 90%, and 75% *Cistanche* at concentrations of 100 µg/ml. These effects were characterized by an increased general activity, a strengthening in burst structure and a strengthening in the synchronicity.

Figure 1C:
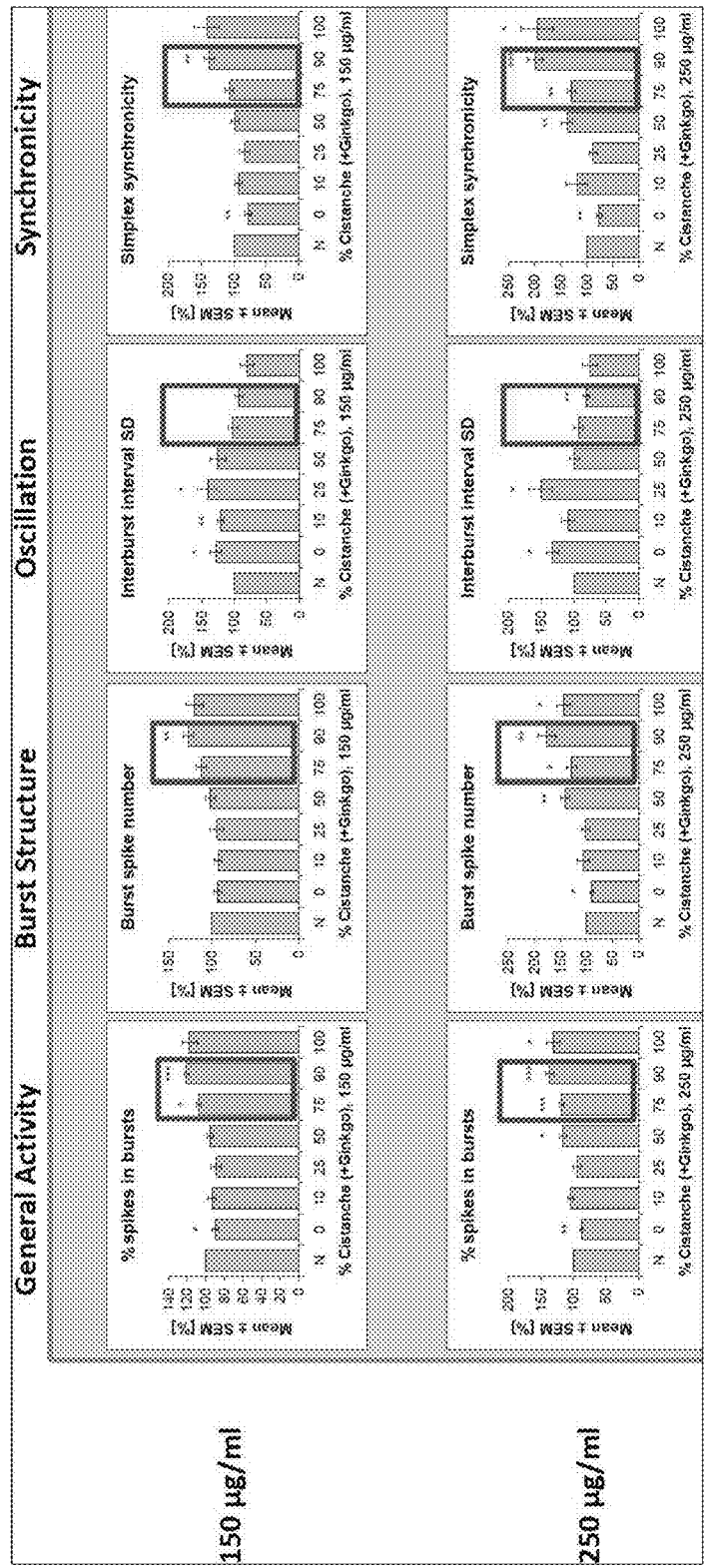
FIG. 1C depicts bar charts of further acute application examples.

FIG. 1C further depicts acute application examples, specifically bar charts showing that the enhancing effects increased with rising *Cistanche* concentrations up to 250 µg/ml.

Figure 1D:
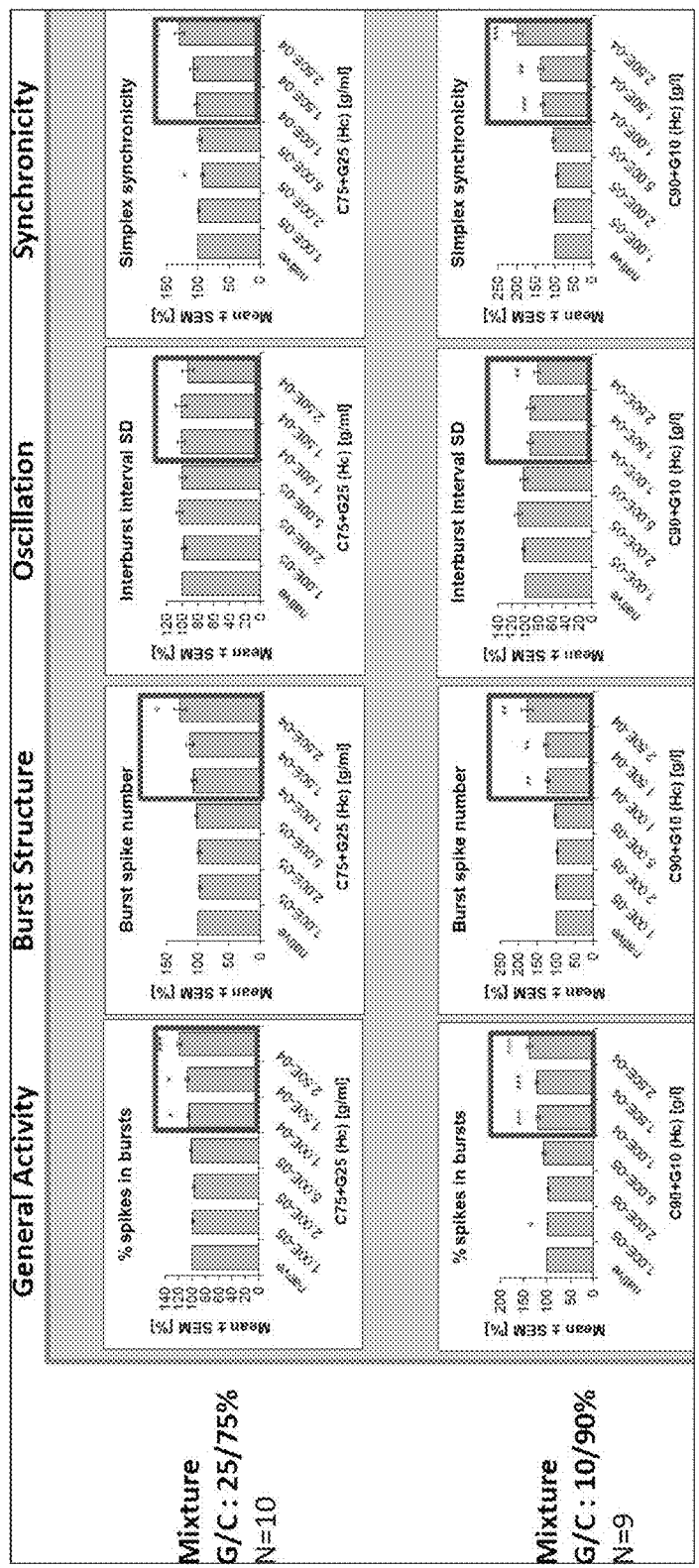
FIG. 1D depicts bar charts of further acute application examples.

FIG. 1D further depicts acute application examples, specifically bar charts from the isobolographic analysis of *Ginkgo* ("G"), *Cistanche* ("C"), and the five mixtures thereof showing that the 25%/75% (G:C) and even more so the 10%/90% (G:C) mixtures of *Ginkgo/Cistanche* appear to have potentiating effects of the network simulation at concentrations of 100 µg/ml, 150 µg/ml, and 250 µg/ml.

Results: Chronic Application

Figure 2:
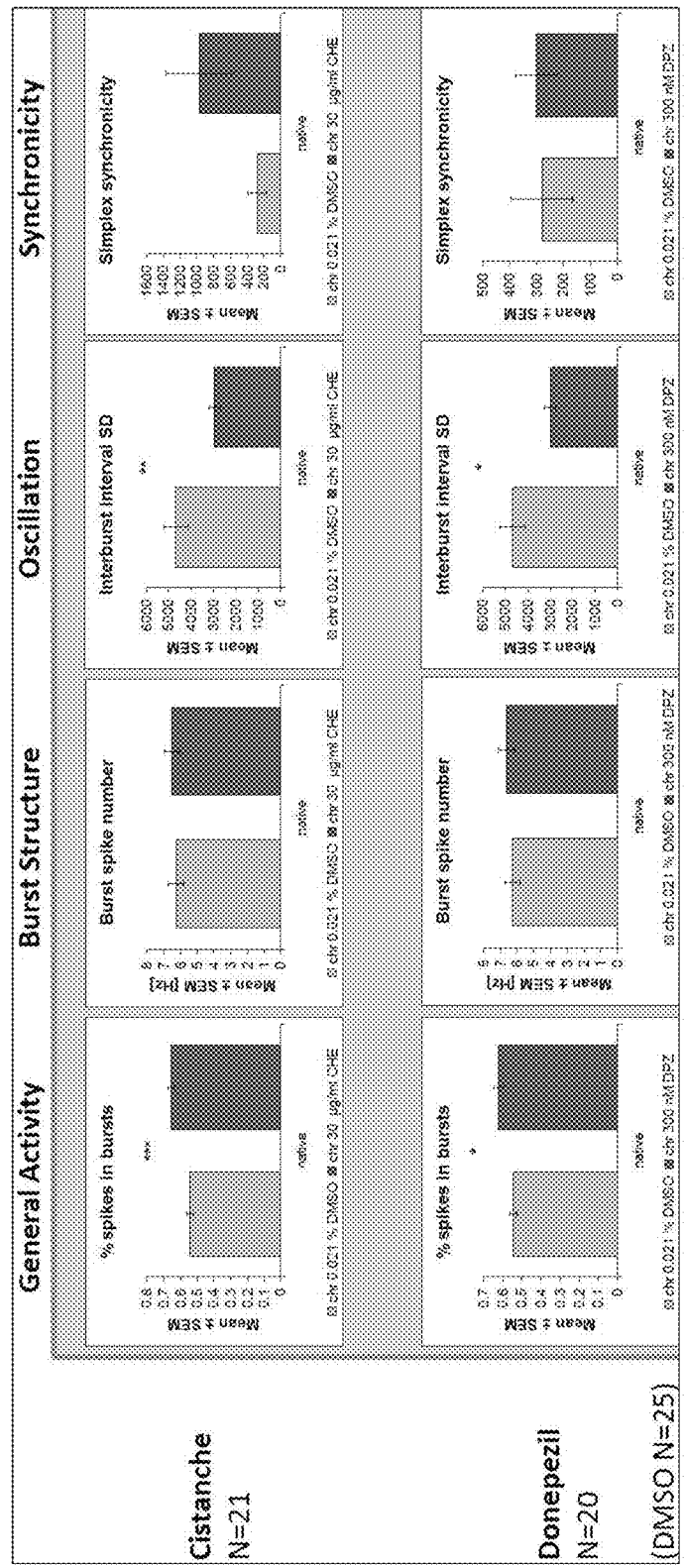
FIG. 2 depicts bar charts of chronic application examples.

FIG. 2 depicts chronic application examples, specifically bar charts that show that the chronic treatment of hippocampal cultures with 300 nM Donepezil ("DPZ") or 30 µg/ml *Cistanche* ("CHE") during 4-28 days in vitro enhanced the spontaneous network activity in both treatment groups. However, *Cistanche* induced stronger activity changes than Donepezil.

Figure 3:
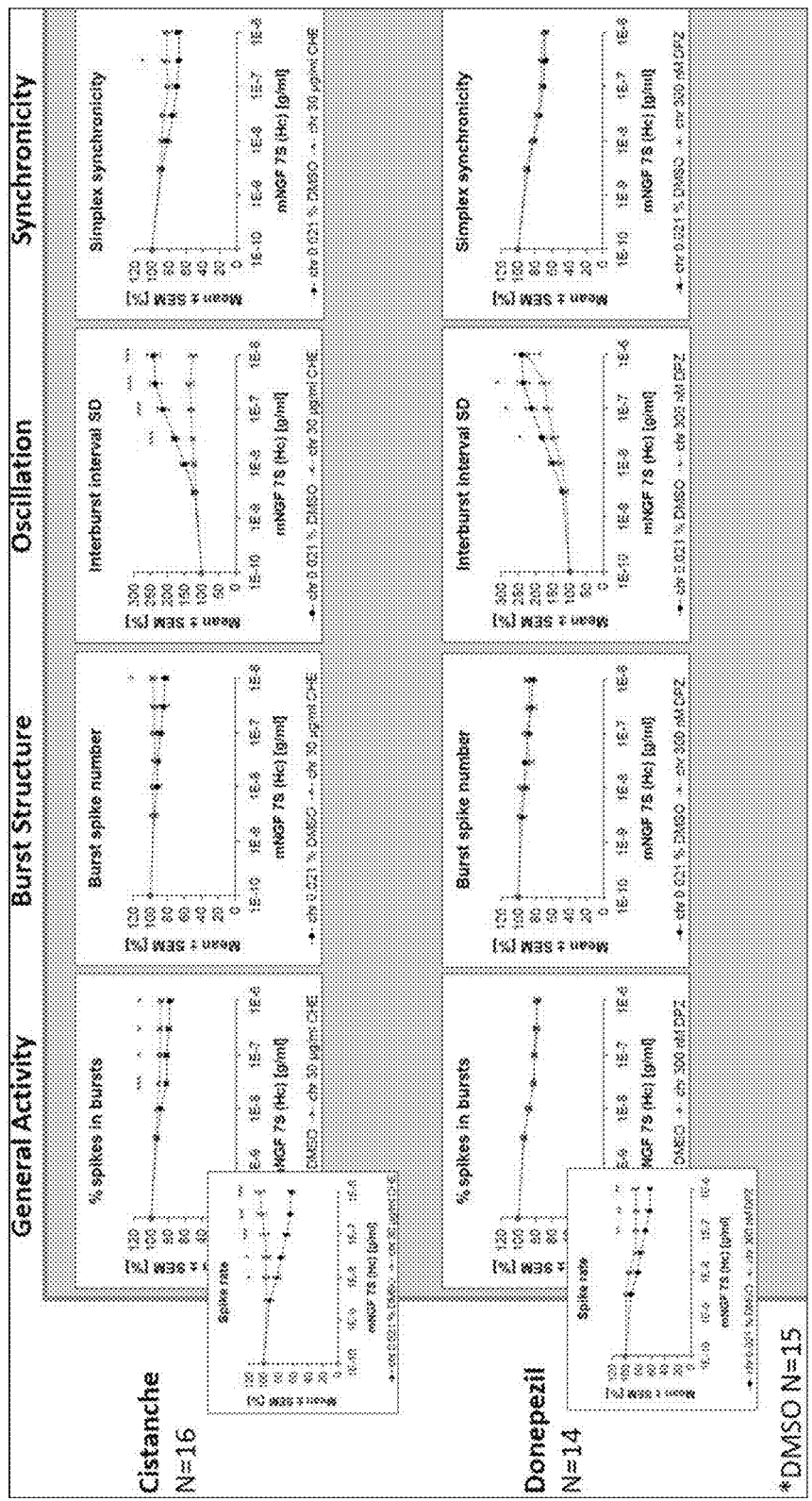
FIG. 3 depicts line graphs of chronic application examples.

FIG. 3 further depicts chronic application examples, specifically line graphs that show that chronic treatment of hippocampal cultures with 300 nM Donepezil or 30 µg/ml *Cistanche* during 4-28 days in vitro compensated the inhibitory acute NGF response. However, *Cistanche* induced a stronger acute compensation of NGF effects than Donepezil.

Figure 4:
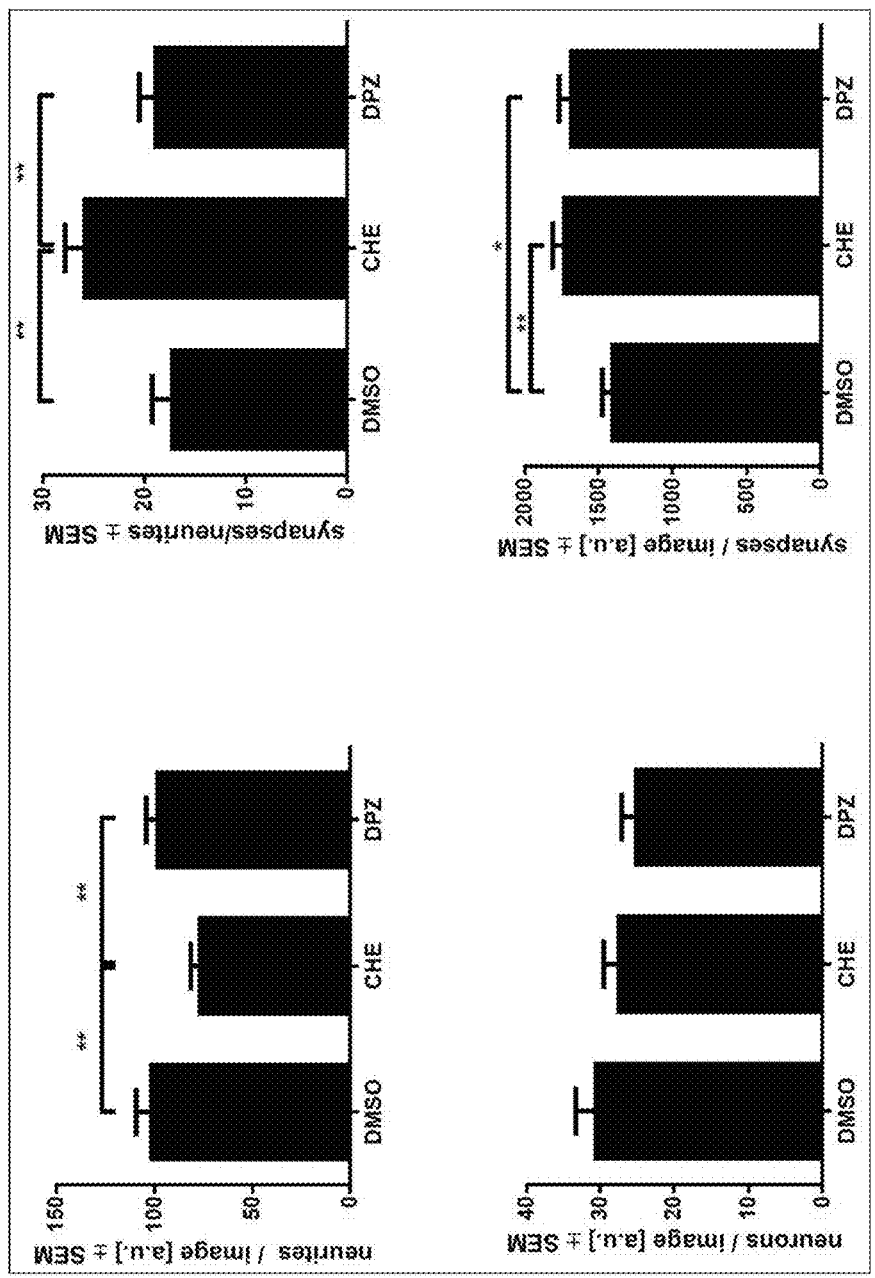
FIG. 4 depicts bar charts of chronic application examples.

FIG. 4 further depicts chronic application examples, specifically bar charts that show that the chronic treatment of hippocampal cultures with 300 nM Donepezil or 30 µg/ml *Cistanche* during 4-28 days in vitro induced an increase in global synapse numbers. However, only *Cistanche* relatively increased the number of synapses per neurite.

Figure 5A:
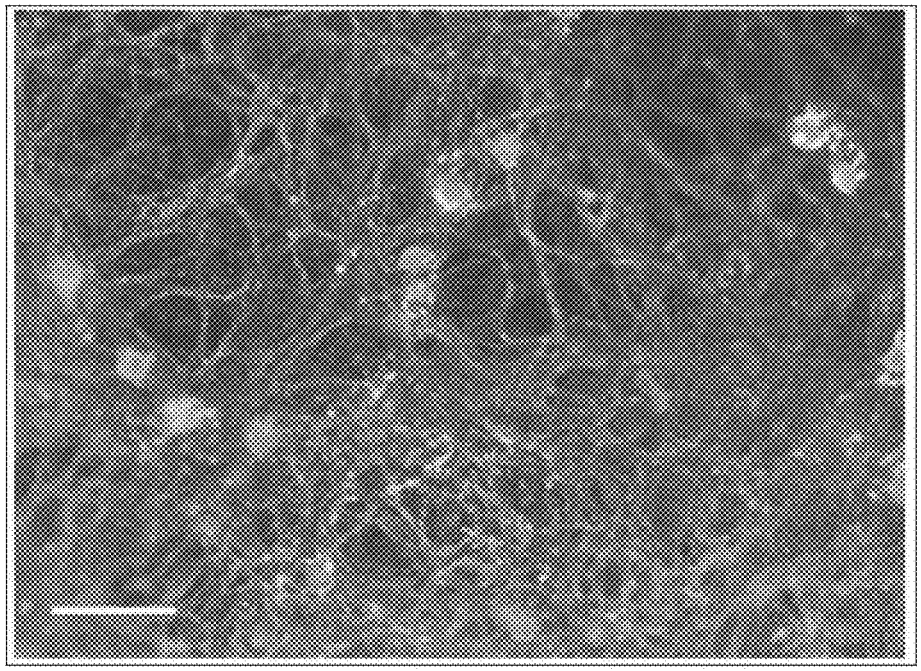
FIG. 5A is an image associated with semi-automatic quantification of examples.

FIG. 5A is an example image associated with semi-automatic quantification of neurons/image, neurites/image, synapses/image, and synapse/neurite ratio. The image depicts color-merge of synapse (green), neurites (red), nuclei (blue), bar=50 µm.

Figure 5B:
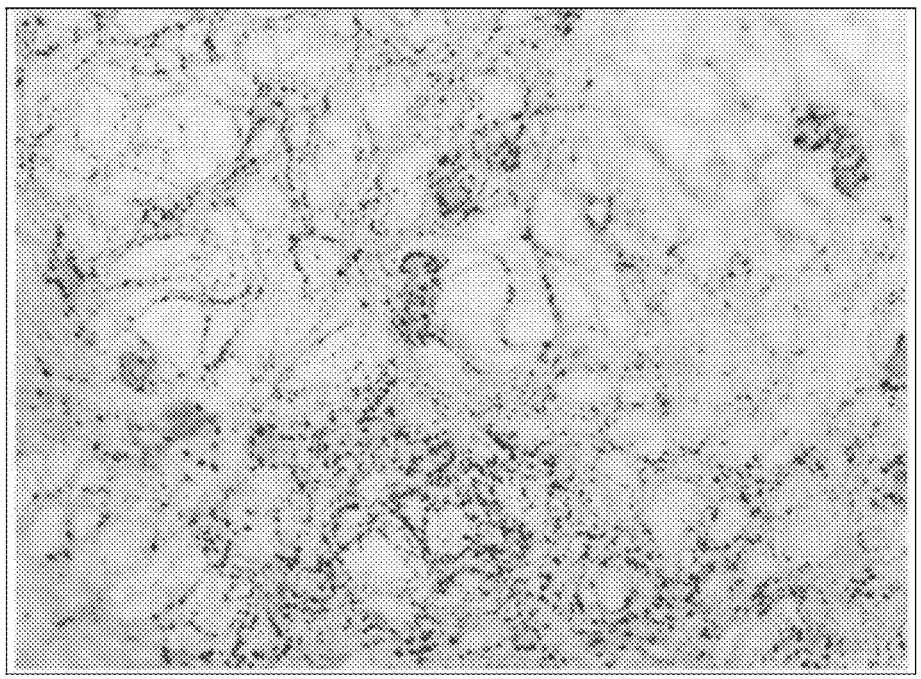
FIG. 5B is an image corresponding to synapse channel for examples.

FIG. 5B is an example image corresponding to synapse channel: color-inverted and analyzed for synapse particles (red labeled after automatic threshold, particle separation and size filter).

Methods

Research focused on the enhancement of neuronal network activity suggestive of memory enhancement, through the evaluation of herbal extracts (i.e., *Ginkgo* and *Cistanche*). The method generally included the four steps outlined below.

Step 1: Acute Study to Assess Effective Concentration Range

Primary mixed neuron/glia cultures from frontal cortex and hippocampus are plated onto MEA neurochips and cultured for at least four weeks. Acute application: effects of interaction between *Cistanche* and *Ginkgo* are analyzed for mixtures with different percentages of *Cistanche* (10-90%) and *Ginkgo* (the remainder) in addition to each alone.

Figure 6:
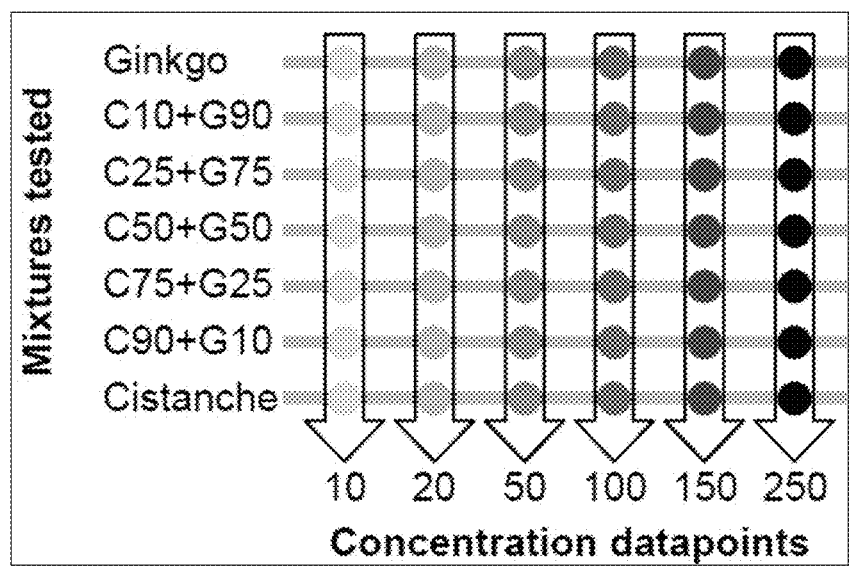
FIG. 6 illustrates examples of an acute study to assess mixtures of *Cistanche* and *Ginkgo* and effective concentration range.

FIG. 6 illustrates examples of the acute study to assess effective concentration range. Seven different concentration response series (vertical) were performed, all with the same five concentrations (horizontal).

Step 2: Assess Combinatorial Effects of *Ginkgo* and *Cistanche*

Figure 7A:
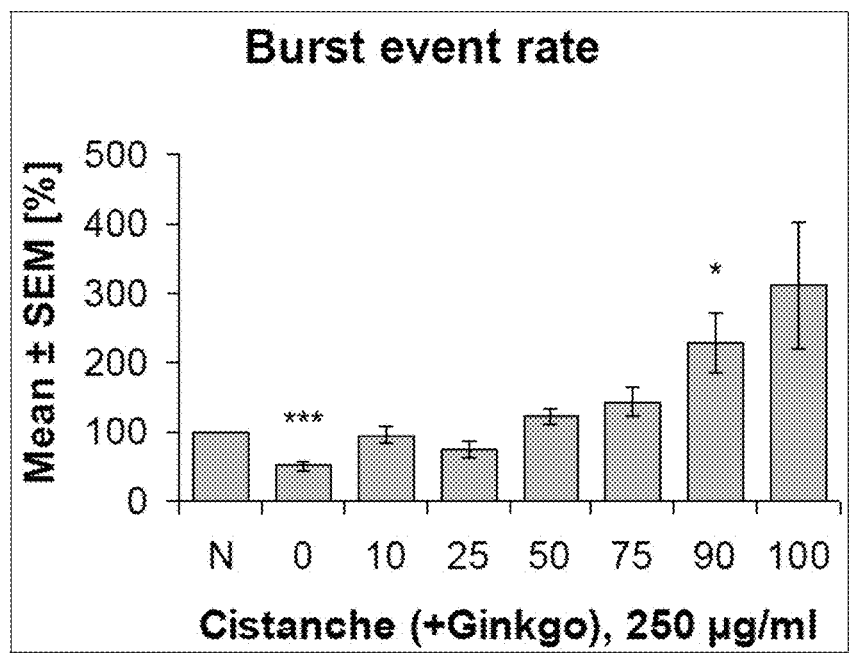
FIG. 7A is a bar chart of examples of a study to assess combinatorial effects of *Cistanche* and *Ginkgo*.

FIG. 7A illustrates examples of the study to assess combinatorial effects of *Ginkgo* and *Cistanche*, specifically a bar chart based on data points from all mixtures for one concentration at a time (native=100%). This Figure generally shows statistics versus "native".

Figure 7B:
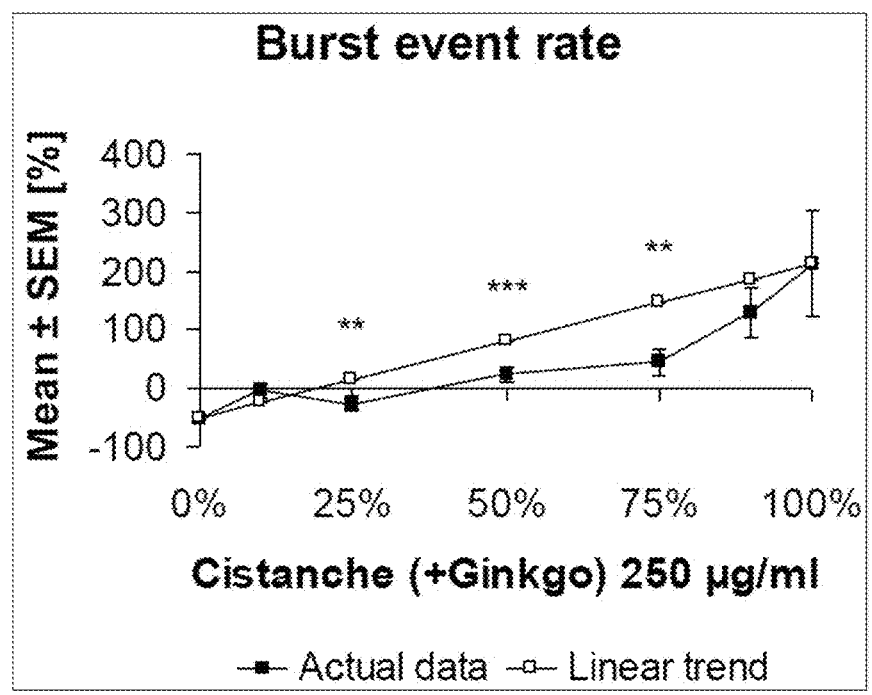
FIG. 7B is a line graph of examples further illustrating the study to assess combinatorial effects of *Cistanche* and *Ginkgo*.

FIG. 7B further illustrates examples of the study to assess combinatorial effects, specifically a line graph based on data points from all mixtures for one concentration and a hypothetical linear trend between *Ginkgo* and *Cistanche* (Native=0%). This Figure generally shows statistics versus linear trend.

Figure 7C:
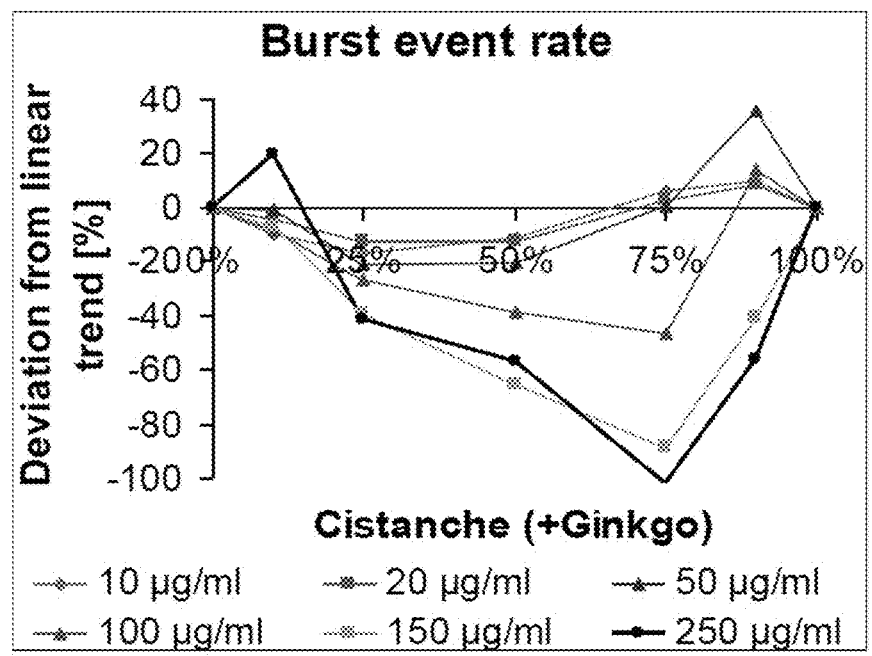
FIG. 7C is a line graph of examples further illustrating the study to assess combinatorial effects of *Cistanche* and *Ginkgo*.

FIG. 7C further illustrates examples of the study to assess combinatorial effects, specifically a line graph directed toward detrending data, yielding the difference relative to the trend, and overlaying all mixtures.

Figure 8:
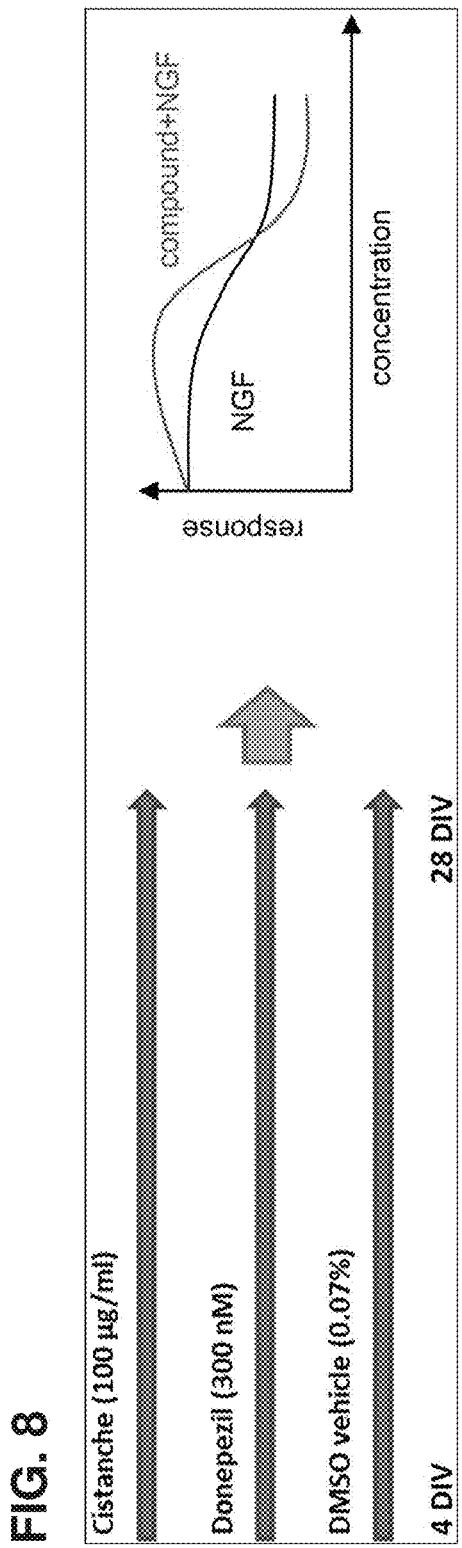
FIG. 8 illustrates examples of a study to assess chronic effects of *Cistanche tubulosa* extract on maturation of a neuronal network.

Step 3: Assess Chronic Effects of *Cistanche tubulosa* Extract on Maturation of a Neuronal Network FIG. 8 illustrates examples of the study to assess chronic effects of *Cistanche tubulosa* extract on maturation of a neuronal network. Hippocampal cultures on MEA neurochips were treated with 30 µg/ml *Cistanche*, 300 nM Donepezil, or a dimethyl sulfoxide ("DMSO") vehicle control. At 28 days after repeated dose chronic treatment, spontaneous activity was measured, followed by recording of activity to acute NGF concentration-response curve.

Step 4: Immuno-Histochemical Analysis

Figure 9:
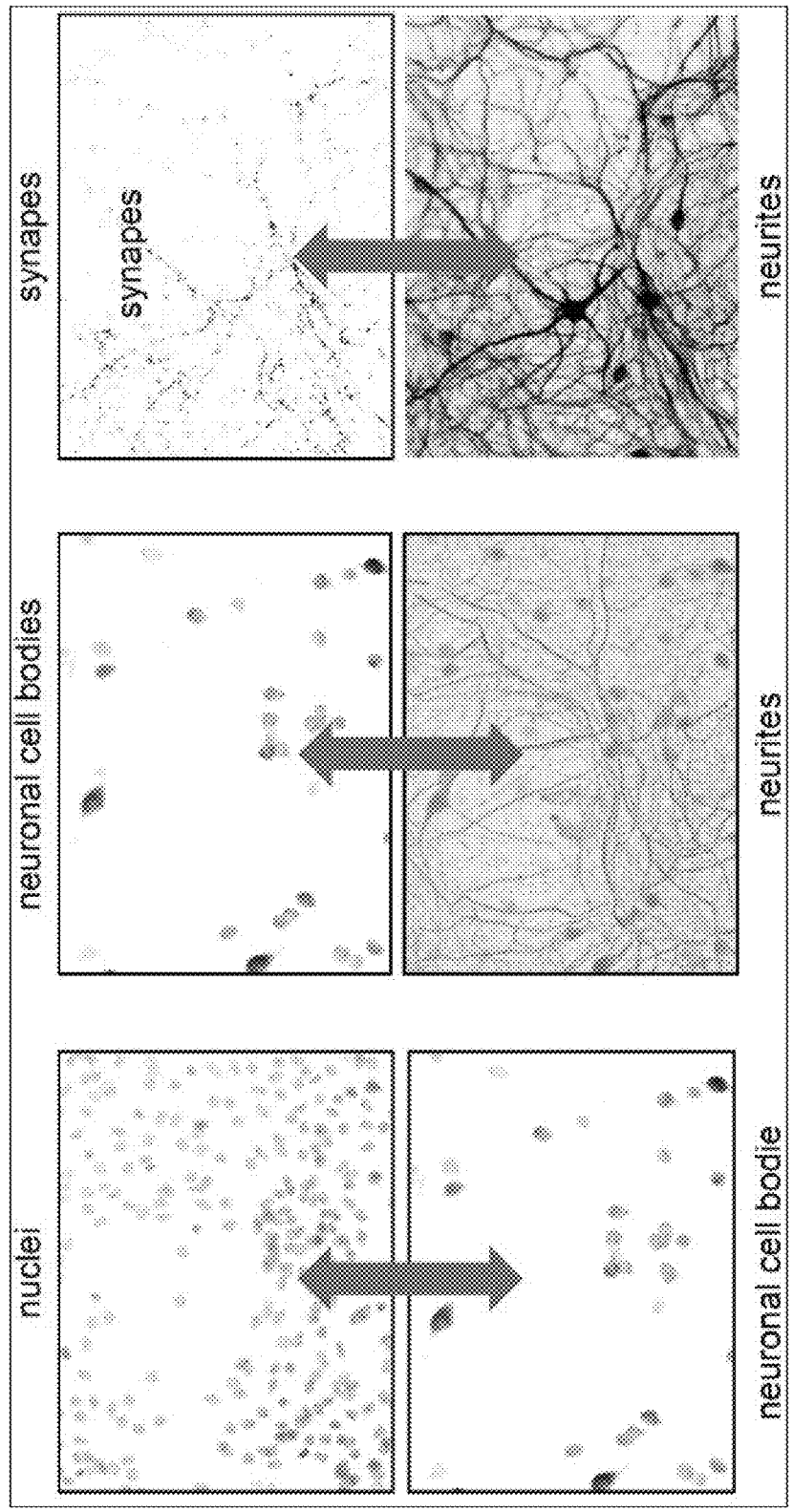
FIG. 9 illustrates examples of a study directed at immunohistochemical analysis.

FIG. 9 illustrates examples of the study directed at immuno-histochemical analysis. Recorded cultures are further analyzed by immunocytochemistry, fluorescence microscopy and semi-automatic quantitative image analysis. Images are quantified per image for: cell number, neuronal number, neurite number, synapse number, % neurons, neurites per neuron, and synapses per neuron.

HPLC Fingerprinting

Figure 10:
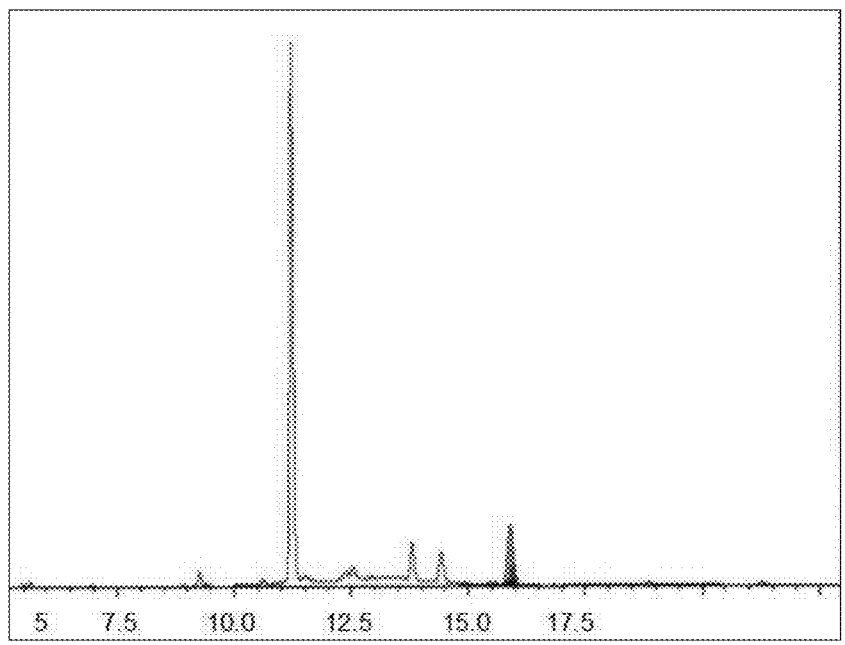
FIG. 10 illustrates a *Cistanche tubulosa* fingerprint.

FIG. 10 illustrates a *Cistanche tubulosa* fingerprint. Specifically, standardization of *Cistanche tubulosa* using high-performance liquid chromatography ("HPLC"). The extract is standardized to 70% phenylethanoid glycosides (composed of at least 25% echinacoside, acetoside, isoacteoside, and verbacoside).

Figure 11:
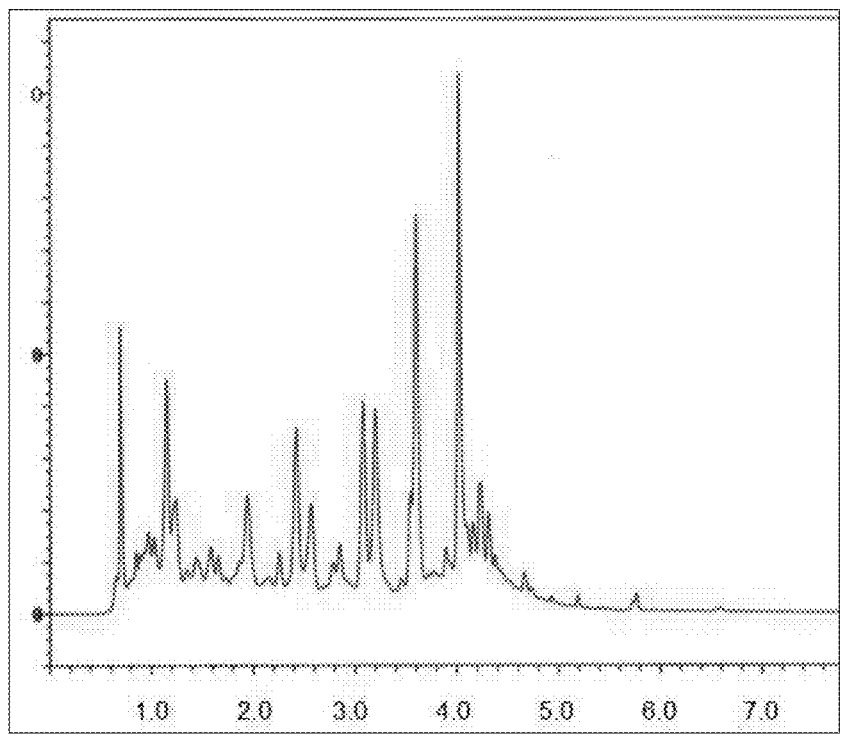
FIG. 11 illustrates a *Ginkgo biloba* fingerprint.

FIG. 11 illustrates a *Ginkgo biloba* fingerprint. Specifically, standardization of *Ginkgo biloba* using HPLC. The extract is standardized to 24% flavone glycoside and 6% terpene lactones.

Phenotypic Screening with MEA Neurochips

MEA neurochip recordings were used to evaluate activity changes in hippocampal networks elicited by various concentrations and combinations of two cultivated, standardized extracts of CT and GB, with and without acute application of NGF.

Figure 12:
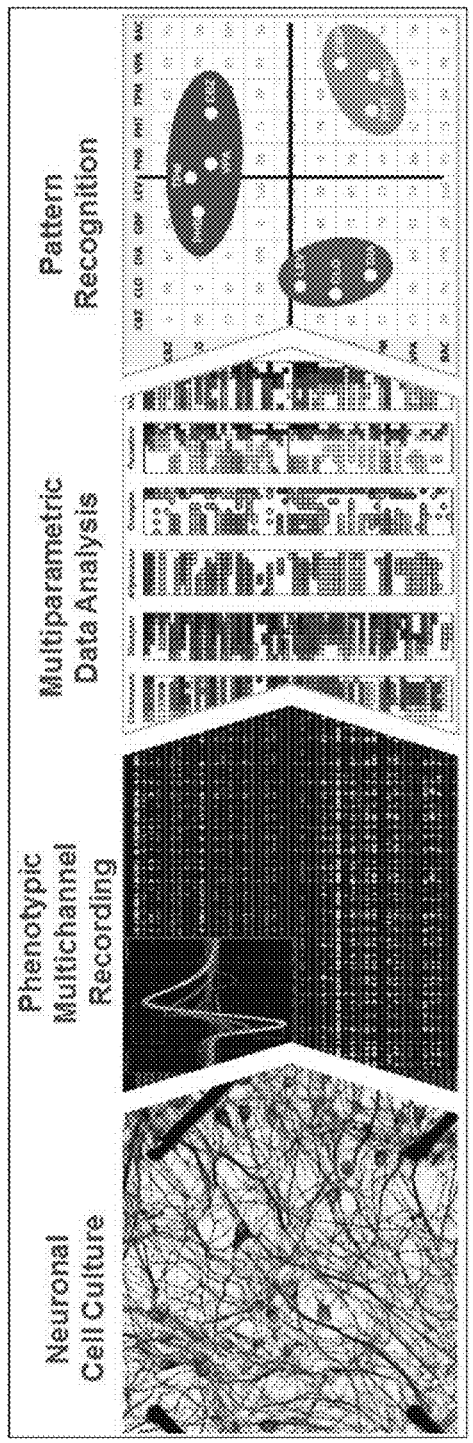
FIG. 12 illustrates steps of a phenotypic screening process.

FIG. 12 illustrates steps of a phenotypic screening process utilizing MEA neurochips. The steps include: 1) neuronal cell culture; 2) phenotypic multichannel recording; 3) multi-parametric data analysis; and 4) pattern recognition. Each of these steps/aspects of FIG. 12 is detailed below.

1) Primary murine cell culture: Frontal Cortex, Hippocampus, and Hypothalamus.

2) Network spike trains and single neuron action potential. High resolution of spatio-temporal network activity patterns.

3) 200 activity parameters: General Activity; Burst Structure; Synchronicity/Connectivity; and Oscillation. Specific in vitro assays with compound or disease related parameter selection.

4) Database with functional fingerprints of over 100 basic and clinically compounds. Similarity and differentiation from known compound effects. Combination effects.

Figure 13:
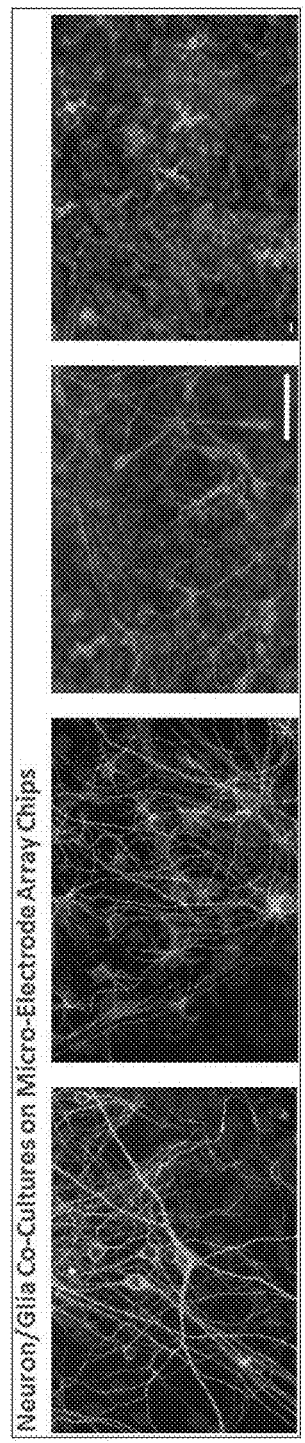
FIG. 13 depicts various neuron/glia co-cultures.

FIG. 13 depicts neuron/glia co-cultures on MEA neurochips. The leftmost image depicts GABAA receptor (alpha1, red), Neurons (TuJ, green), and nucei (blue); the second image from left depicts Neurons, neuronal somata (HuCD, red), and nuclei; the second image from right depicts Oligodendrocytes (O4, red), Neurons, and nuclei; and the rightmost image depicts Astrocytes (GFAP, red), microglia (Lectin, green), and nuclei.

Characterization: Co-cultures of neurons and glial cells in serum-containing media e.g. cell populations in frontal cortex cultures on MEA neurochips (28 div): neurons (~20%), astrocytes (~70-80%), microglia (~1-2%), oligo-dendrocytes (present, neglectable).

Figure 14:
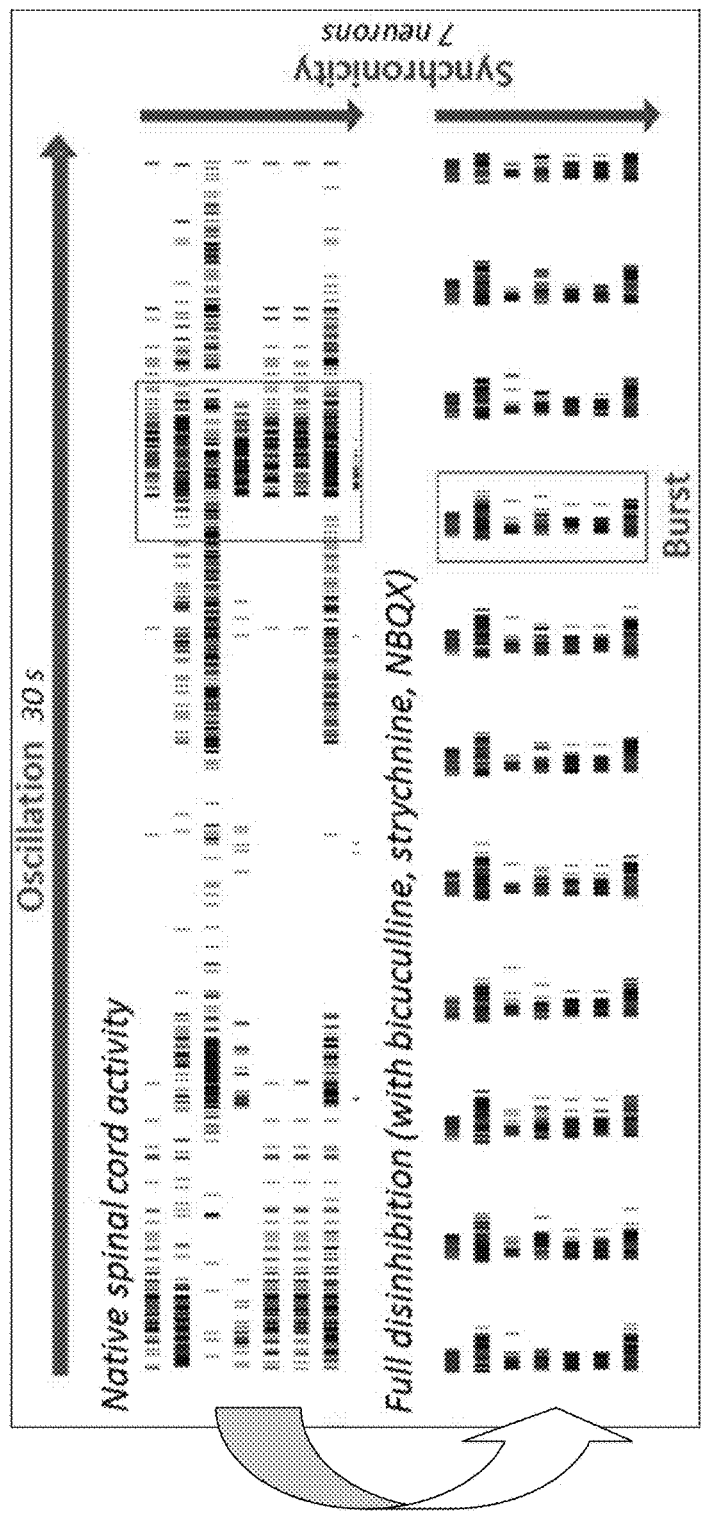
FIG. 14 illustrates multi-parametric characterization of neuronal network activity.

FIG. 14 illustrates multi-parametric characterization of neuronal network activity.

Read out: Extracellular action potentials on single neuron and network activity level; spatio-temporal network activity changes in time scales of spikes and bursts. Spike train is described by 200 activity parameters in four categories: 1. General Activity, e.g. spike rate, burst rate, burst period, and percent of spikes in burst; 2. Burst Structure, e.g. number, frequency and ISI of spikes in bursts, burst duration, amplitude, area, plateau position, and plateau duration; 3. Oscillation, e.g. variation over time as an indicator for the strength of the oscillation; Gabor function fitted to autocorrelograms; and 4. Synchronicity/Connectivity, e.g. variation within the network as an indicator for the strength of the synchronization, simplex synchronization, and percent of units in synchronized burst.

Acute Application of *Ginkgo biloba* and *Cistanche tubulosa*

Comparison of the acute concentration-dependent effects induced by A) GB and B) CT and their respective DMSO control concentrations on hippocampus network activity in vitro. Displayed are six activity describing parameters in four categories (general activity, burst structure, oscillation, and synchronization) for treatment of nine concentrations from 10 pg/ml to 100 µg/ml. (mean±standard error, *Ginkgo*: n=5, *Cistanche*: n=8, DMSO: n=5. Student's unpaired t-test: *p≤0.05; p≤0.01; *p≤0.001).

Figure 15:
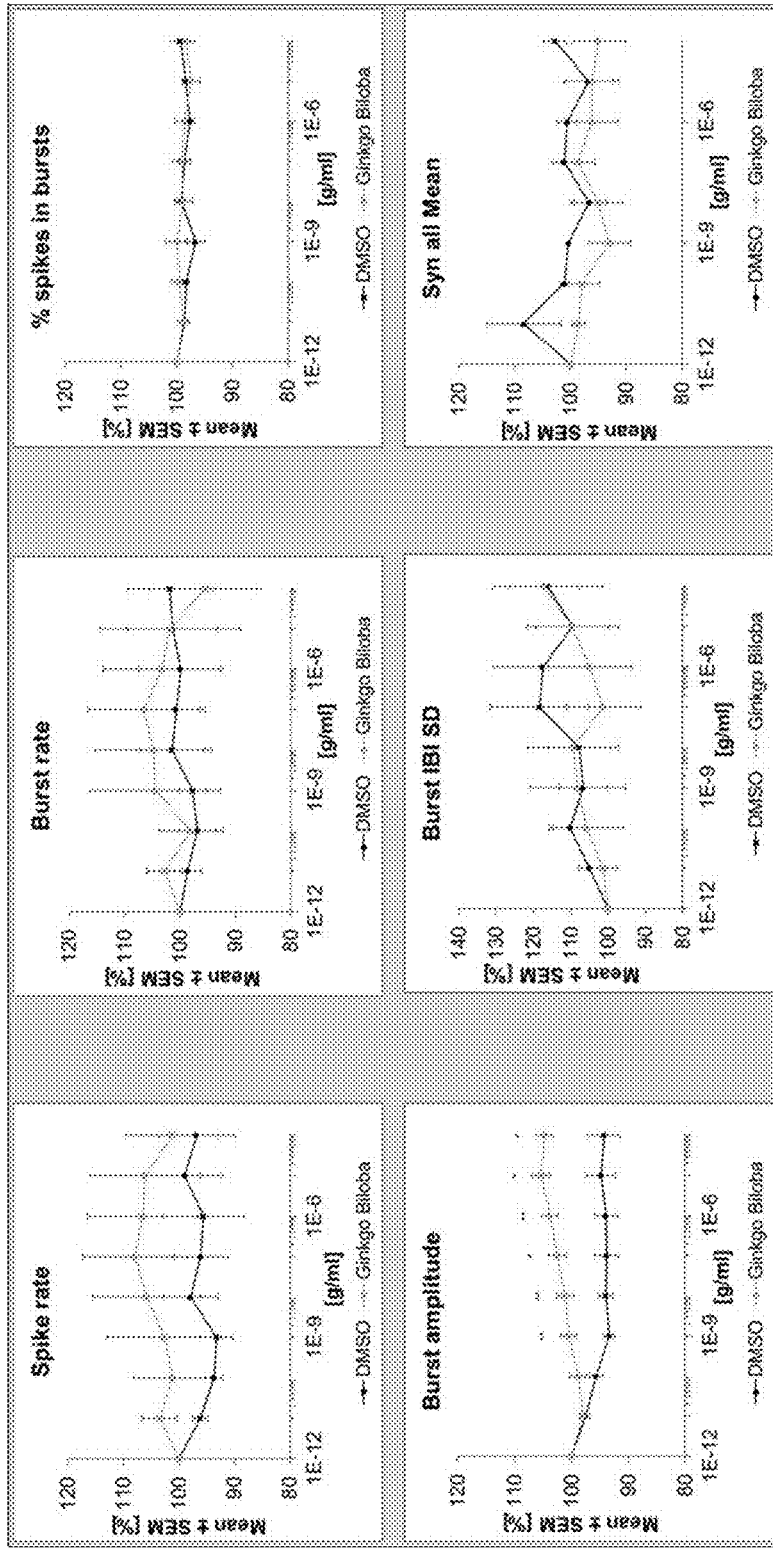
FIG. 15 depicts line graphs of acute application of *Ginkgo biloba* examples.
Figure 16:
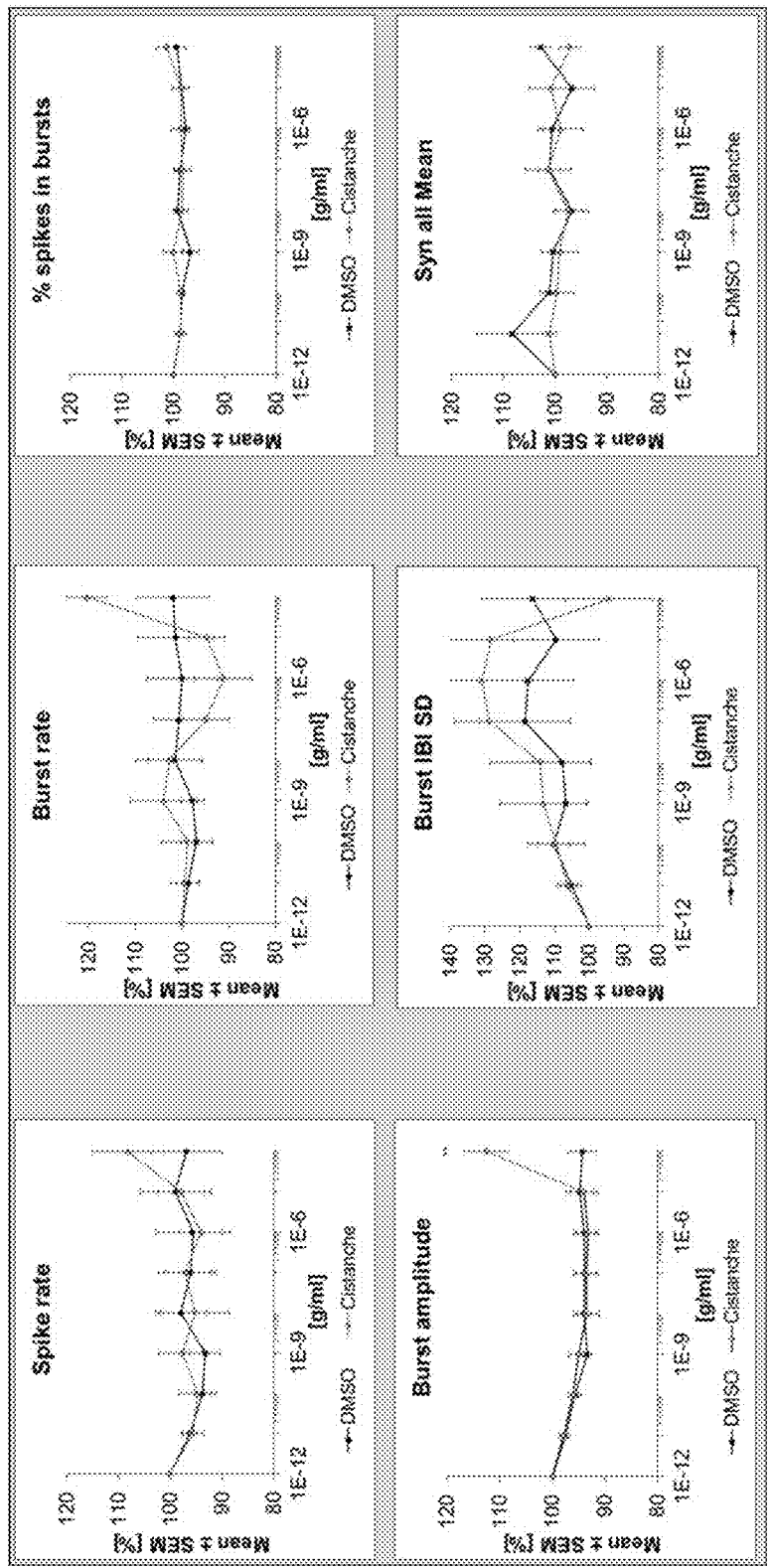
FIG. 16 depicts line graphs of acute application of *Cistanche tubulosa* examples.

FIG. 15 depicts line graphs illustrating that acute application of *Ginkgo biloba* induces a mild concentration dependent activity change in burst structure. FIG. 16 depicts line graphs illustrating that acute application of *Cistanche tubulosa* induces a mild concentration dependent bi-phasic activity change in burst structure.

Isobolographic Analysis

Figure 17:
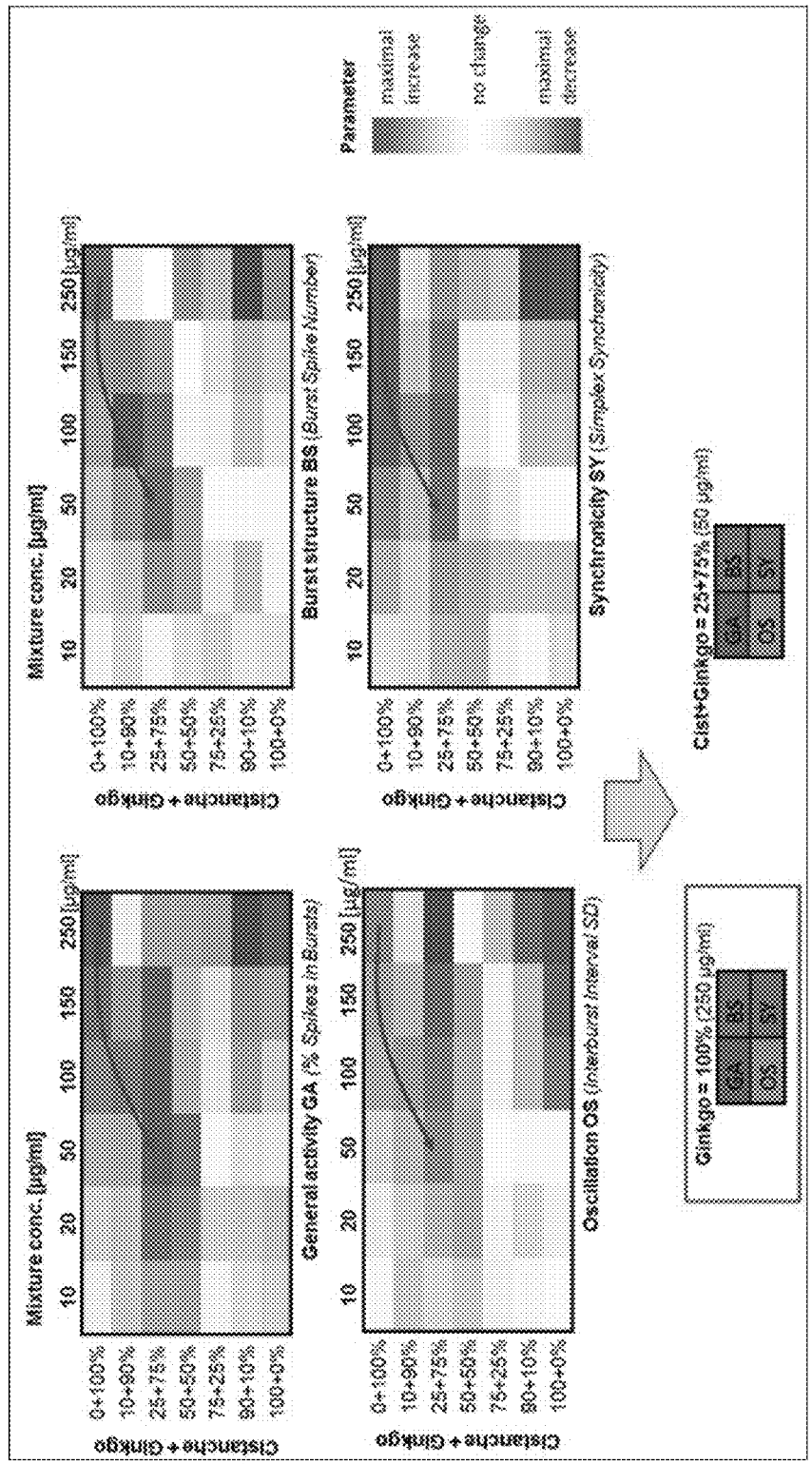
FIG. 17 depicts *Ginkgo* and *Cistanche* mixture and concentration matrices.

FIG. 17 depicts *Ginkgo* and *Cistanche* mixture and concentration matrices associated with general activity ("GA"), burst structure ("BS"), oscillation ("OS"), and synchronicity ("SY").

To make the matrices, data from concentration response curves are color coded as increased or decreased relative to native. Next, results from all mixtures and all concentrations are combined into a matrix. Next, out of 200, the relevant activity features describing GA, BS, OS, and SY are compared to a reference fingerprint.

Higher % of GB induces changes at lower concentrations of total compound. Increasing amounts of GB (>50%) elicited an inhibition of general activity and when GB:CT is 75%/25%, surprisingly the inhibition potency increased five-fold over GB alone. Mixtures with increasing CT potentiated network stimulation, most apparent at 10%/90% GB:CT and 100 µg/ml, 150 µg/ml, and 250 µg/ml.

Chronic Effects

Figure 18A:
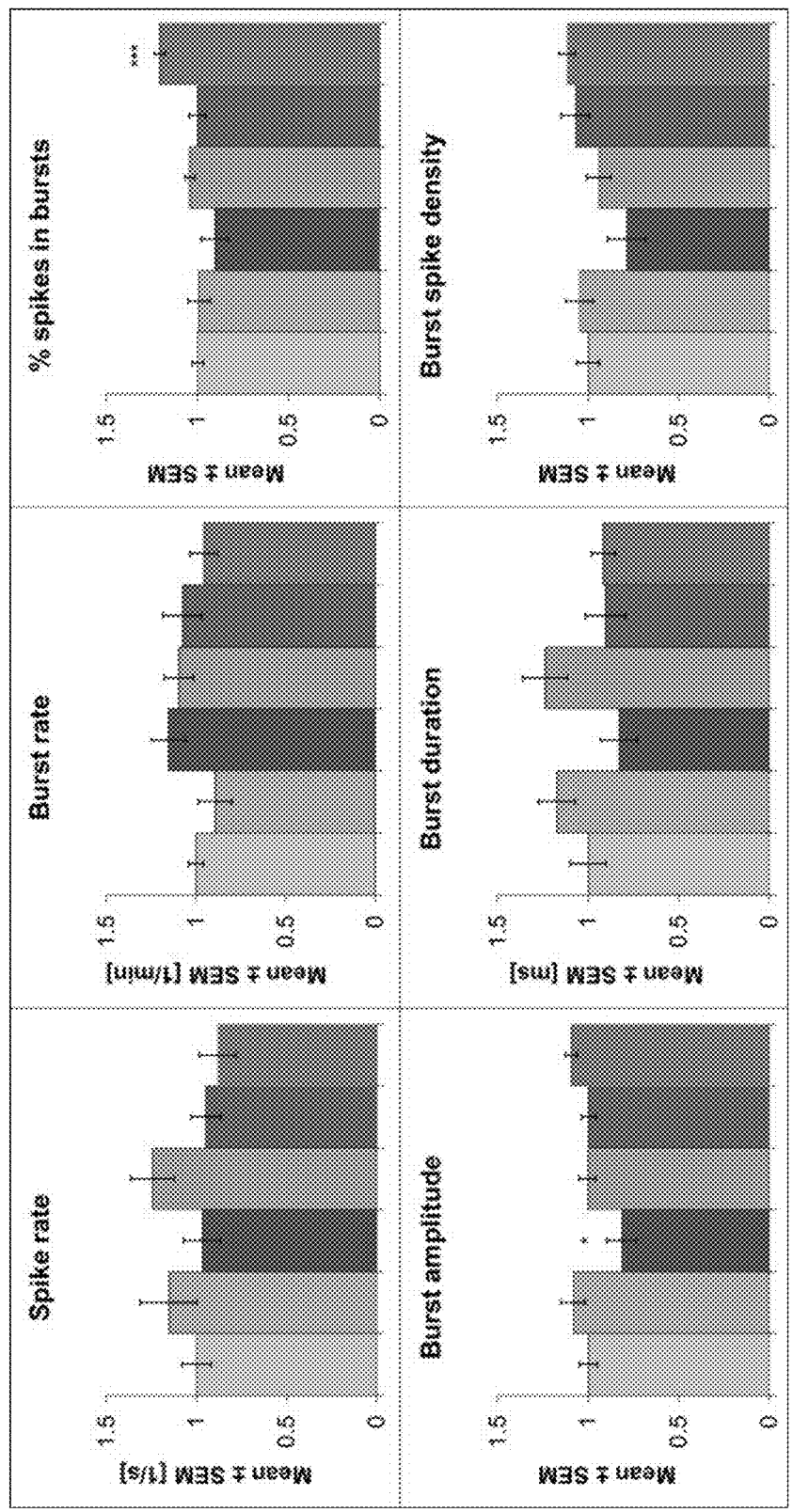
FIG. 18A depicts bar charts illustrating chronic effects of examples.

FIG. 18A depicts bar charts illustrating chronic effects. Specifically, chronic effects on native activity of 30 µg/ml *Cistanche tubulosa* ("CT"), two CT and *Ginkgo biloba* ("GB") mixtures in a ratio of 90%:10% or 70%:30% (each at 10 µg/ml or 30 µg/ml), or 0.021% DMSO vehicle control.

Figure 18B:
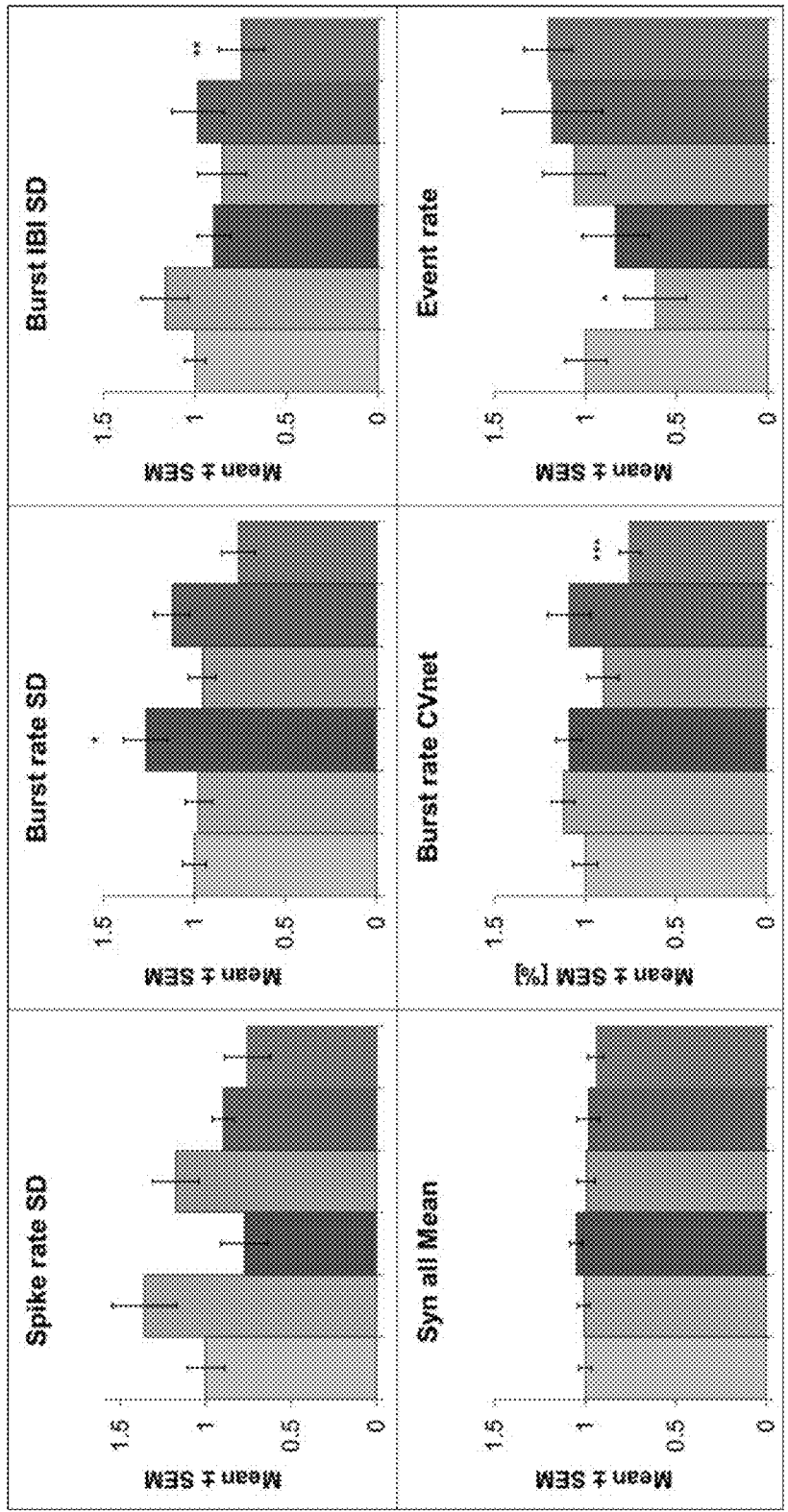
FIG. 18B depicts additional bar charts illustrating chronic effects of examples.

FIG. 18B depicts additional bar charts illustrating the chronic effects. In all of the bar charts, the leftmost bar is 0.021% DMSO, second bar from left is 10 µg/ml at GB10+CT90, third bar from left is 30 µg/ml at GB10+C90, third bar from right is 10 µg/ml at GB30+CT70, second bar from right is 30 µg/ml at GB30+CT70, and rightmost bar is 30 µg/ml at 100% CT. (mean±standard error, student's t-test: *p≤0.05; p≤0.01; *p≤0.001).

CT alone resulted in an enhancement of spontaneous activity through strengthened bursting activity, particularly increase of burst surprise and increase of percentage of total spikes grouped in bursts. Chronic treatment of 10 µg/ml of the 70:30 mixture (CT:GB) caused network activity changes, notably an increase in spike rate, decrease in event rate and loosening of burst structure.

Heat Mapping

Figure 19A:
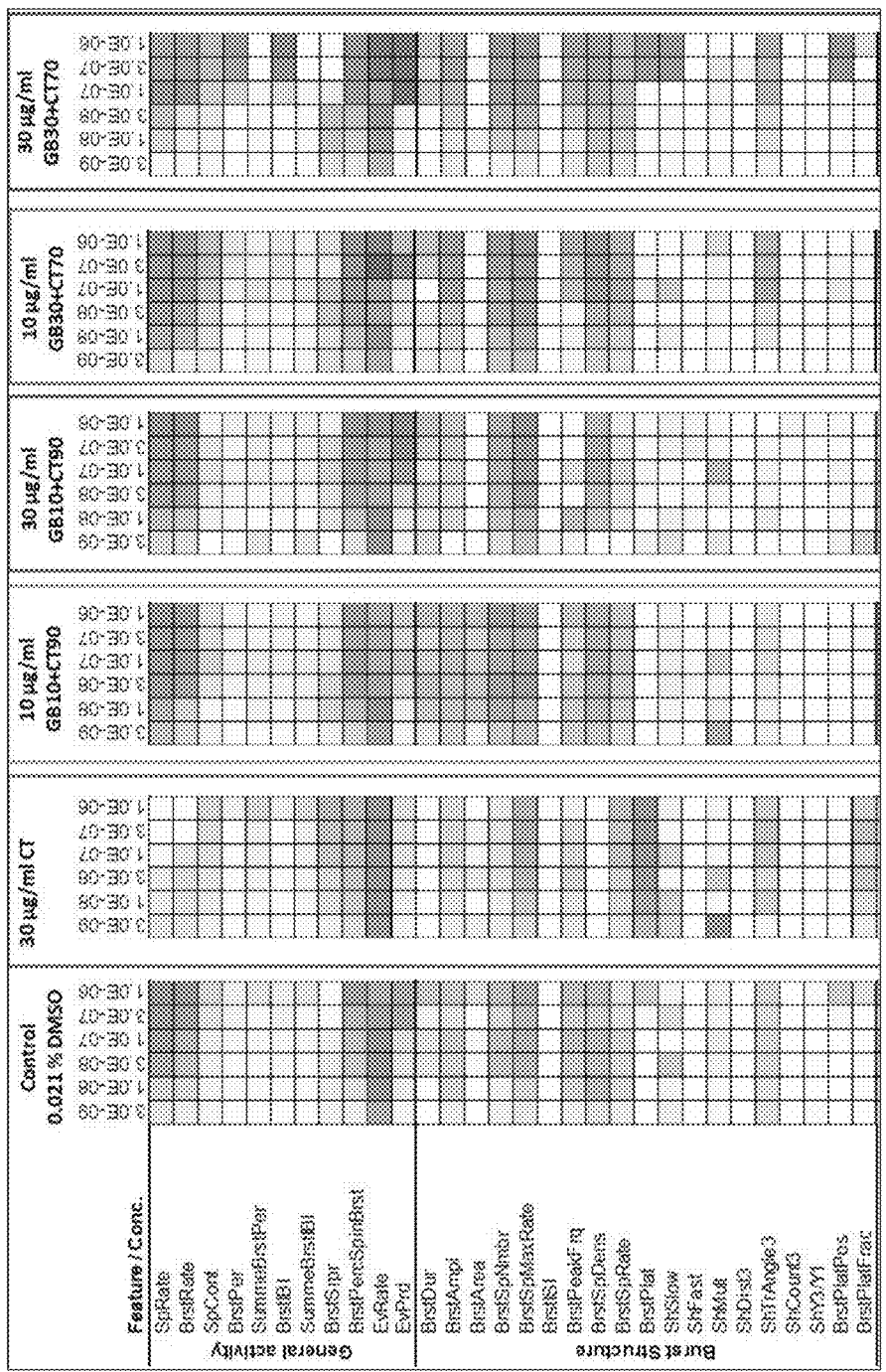
FIG. 19A is a first portion of a heat map.
Figure 19B:
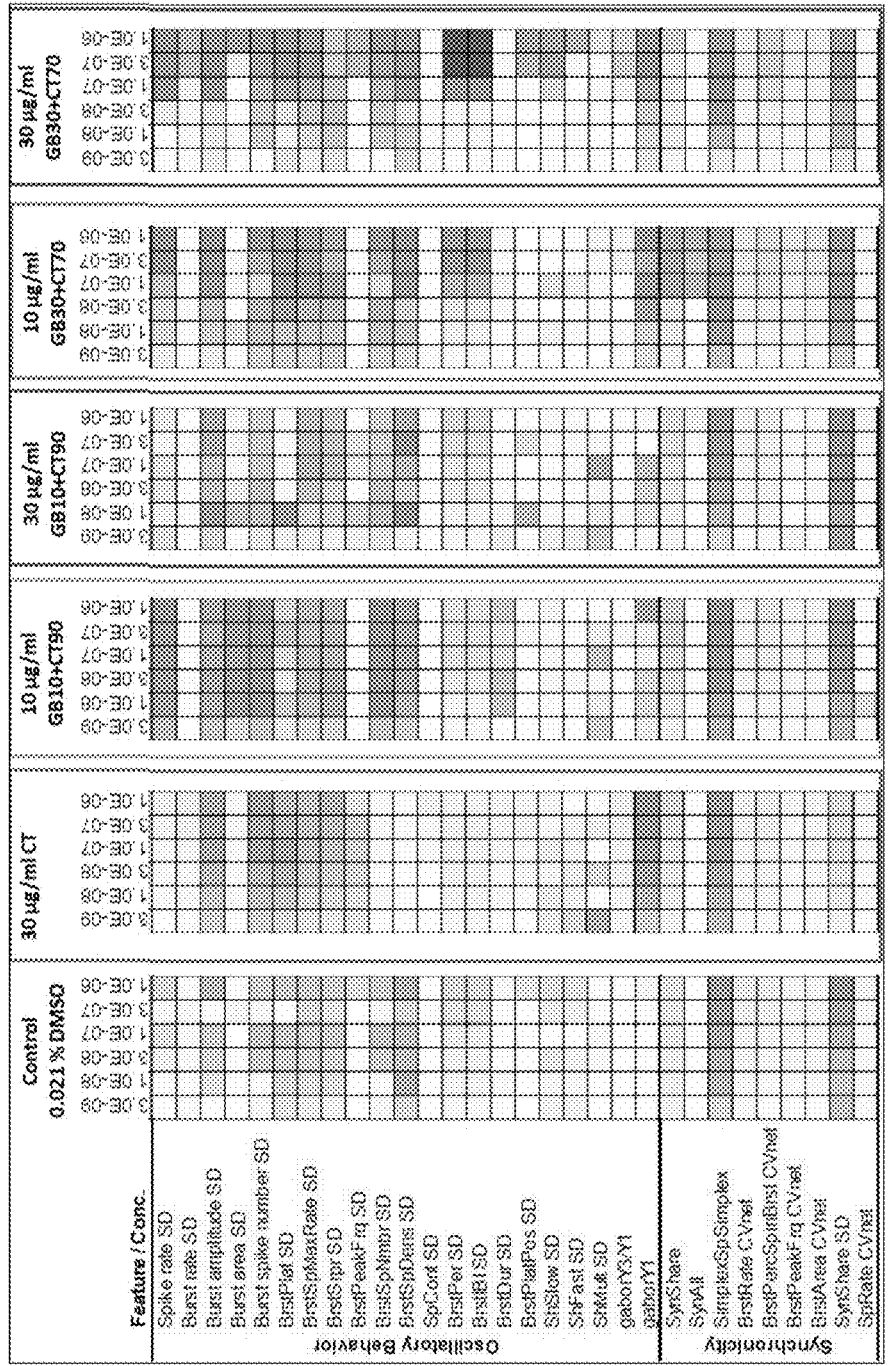
FIG. 19B is second portion of the heat map of FIG. 19A.

FIG. 19A is a first portion of a heat map and FIG. 19B is a second portion of the heat map. The heat map illustrates concentration dependent effects of acute mouse nerve growth factor ("mNGF") on network activity of chronically treated hippocampal cultures with the mixtures or components described above for FIG. 18.

The heat map illustrates significant changes on the 60 most representative parameters for each mNGF concentration, from 3 ng/ml to 1 µg/ml. The color code changes in activity parameters according to the percent changes (100:no change), with yellow/red=an increase and green/blue=a decrease.

NGF alone induced an inhibition of general activity. Chronic CT alone compensated for the inhibition seen after NGF. The mixture of GB30:CT70 at both concentrations evoked the opposite effect from CT alone, as it enhanced the acute mNGF effect.

Effect of Chronic Application

Figure 20B:
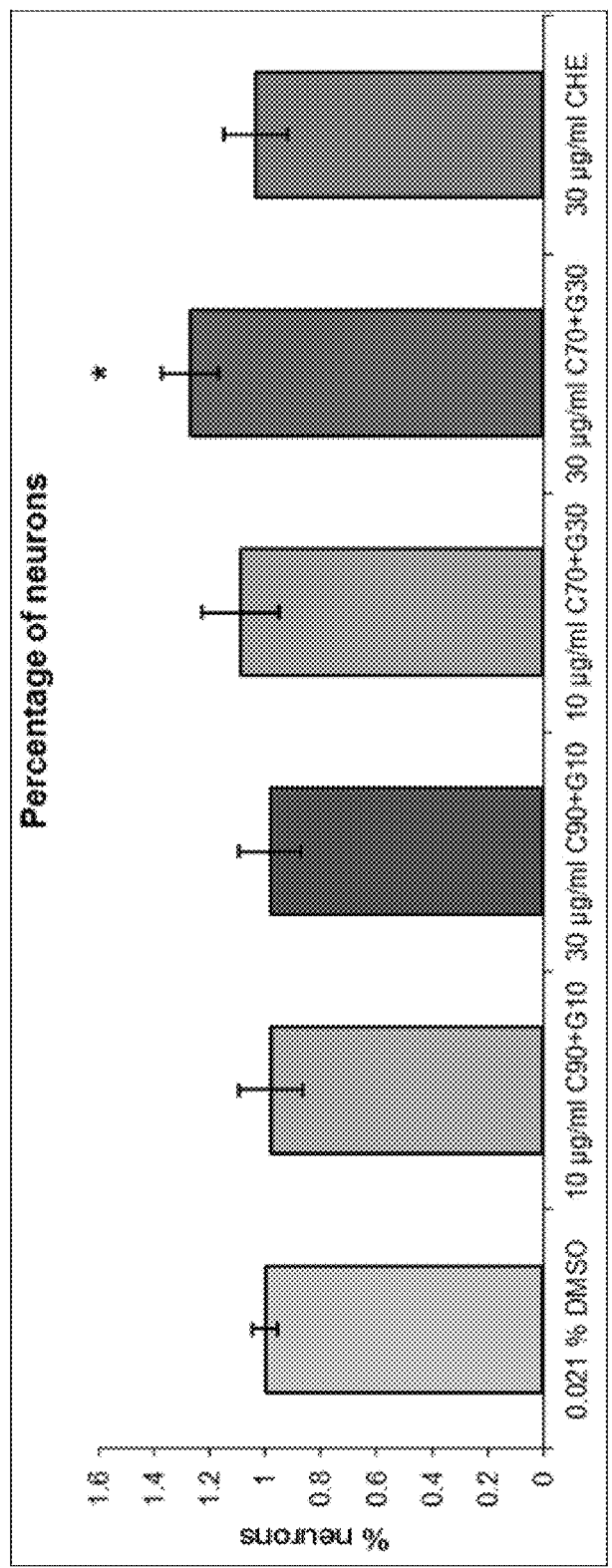
FIG. 20B is a bar chart illustrating chronic application effects on hippocampal network morphology of examples.
Figure 20D:
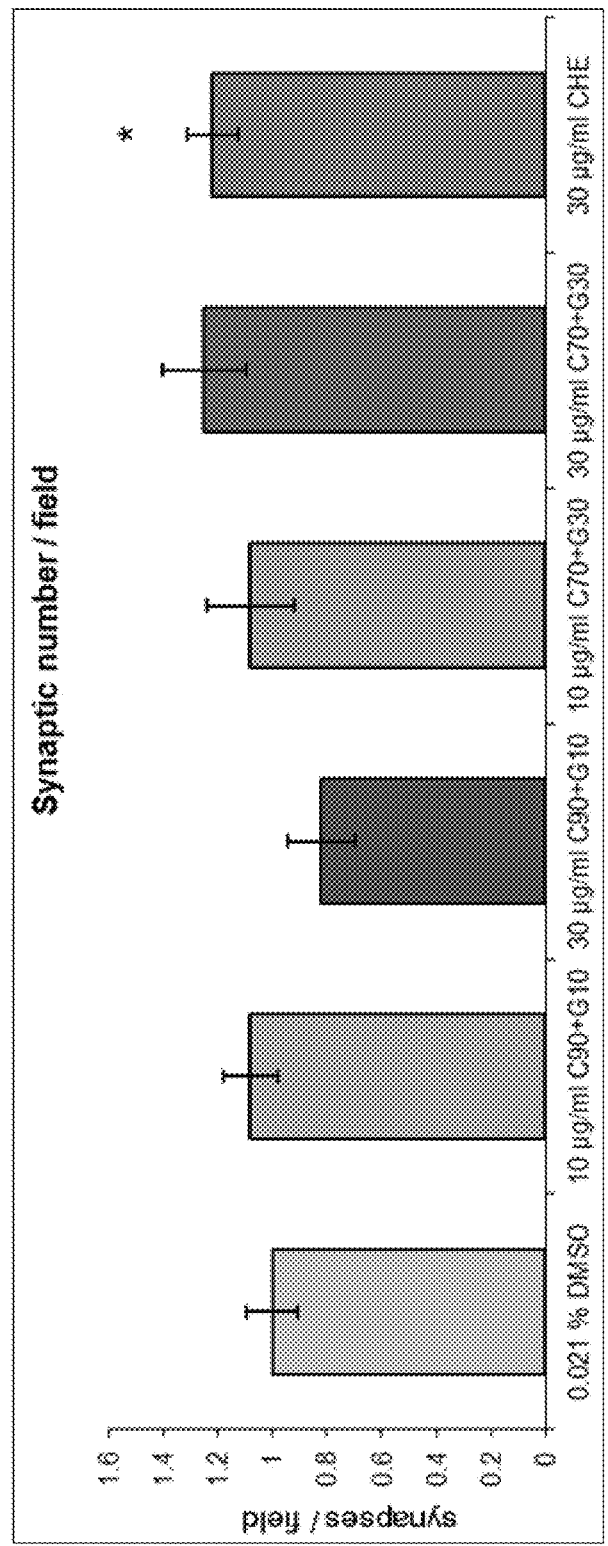
FIG. 20D is a bar chart illustrating chronic application effects on hippocampal network morphology of examples.

FIG. 20A is a bar chart illustrating chronic application effects on hippocampal network morphology with respect to total number of cells/field. FIG. 20B is a bar chart illustrating chronic application effects on hippocampal network morphology with respect to percentage of neurons. FIG. 20C is a bar chart illustrating chronic application effects on hippocampal network morphology with respect to neuritic density. FIG. 20D is a bar chart illustrating chronic application effects on hippocampal network morphology with respect to synaptic number/field. The mixtures or components for FIG. 20 are as described above for FIG. 18.

Recorded cultures were further analyzed by immunocytochemistry, fluorescent microscopy and quantitative image analysis for morphological findings. Semi-automatic quantification (mean±SEM, student's t-test: *$p \leq 0.05$; n=3 with 10-20 images each.)

Figure 21:
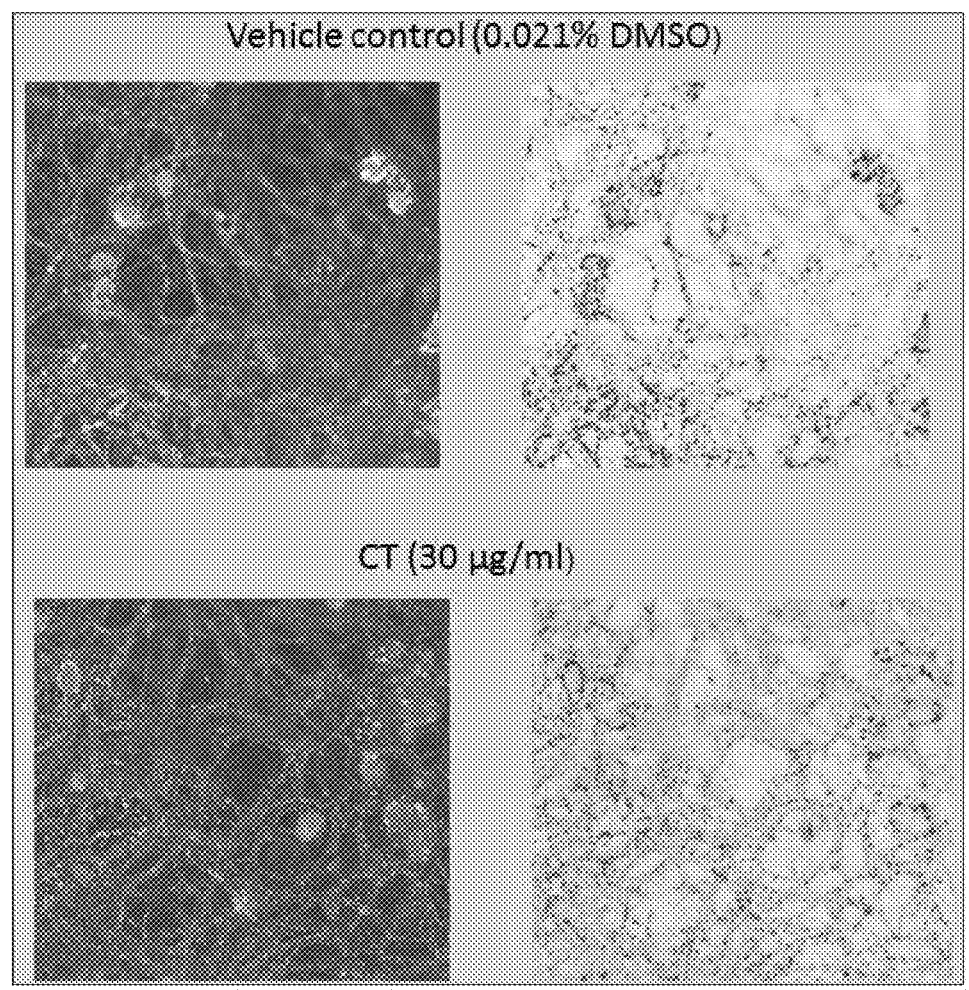
FIG. 21 are images associated with semi-automatic quantification of examples.

FIG. 21 are images associated with semi-automatic quantification of total cells/field, percentage of neurons, neuritic density, and synaptic number/field. The leftmost images correspond to color-merge of synapse (green), neuritis (red), and nuclei (blue). The rightmost images correspond to synapse channel: color inverted and analyzed for synapse particles. After analysis, a higher number or synapses are qualitatively observed in CT 30 µg/ml treated cultures.

CT alone did not increase neuronal cell number, but did increase the number of global synapses as well as the number of synapses per neurite. CT70:GB30 at 30 µg/ml also induced morphological effects shown by an increased percentage of neurons (+27%), and increased number of synapses in relation to the neuritic density increased by 31%.

Summary of Non-Limiting Theories, Examples/Analysis, and Conclusions

Prior to this disclosure, effects of *Cistanche* and *Ginkgo* extracts on neural activity were not clearly elucidated. As described above, MEA neurochip recordings were used to evaluate activity changes in hippocampal networks elicited by various concentrations and combinations of two cultivated, standardized extracts of CT and GB. After acute application to four week old primary hippocampus cultures, multi-parametric analysis revealed both CT and GB induced mild but measurable activity changes within four functional activity categories: GA, BS, OS, and SY.

The isobolographic approach revealed interaction between GB and CT at specific concentrations becoming most apparent at 100 µg/ml when the GB/CT combination is composed of 10-25% GB (remainder CT), with the effects of 10% GB being most pronounced. This concentration and combination increased the spike organization into bursts, induced a stronger BS and increased bursting regularity and SY. Increasing amounts of GB (>50%) elicited an inhibition of GA. Further, when GB:CT is 75/25% potency of GB increased five-fold over GB alone. Mixtures with increasing CT potentiated network stimulation, most apparent at 10%/90% (GB:CT) and 100 µg/ml, 150 µg/ml, and 250 µg/ml.

Chronic CT treatment (30 µl/ml) of hippocampal cultures on MEA neurochips from 4-28 days in vitro resulted in an enhancement of spontaneous activity through strengthened bursting activity. NGF applied acutely to CT treated cultures further increased the response over that of NGF applied to vehicle-treated cultures, notably increasing GA, lengthening burst duration, increasing pattern regularity, and improving SY within the networks.

Recorded cultures were further analyzed by immunocytochemistry, fluorescent microscopy and quantitative image analysis for morphological findings. Chronically treating hippocampal networks with CT did not increase neuronal cell number, but did increase the number of global synapses as well as the number of synapses per neurite. These findings support the notion that CT and GB are neuro-active and interact with endogenous growth factors within neural systems. Further, it has been shown that chronic repeated-dose treatment with CT induced morphological alterations and increased hippocampal network activity in vitro.

Synergistic Effects of *Ginkgo* and *Cistanche* Extracts on Neuronal Activation

The examples above provide scientific evidence to support synergistic interaction between *Ginkgo* and *Cistanche* on neuronal network activity in vitro, and scientifically support the positioning of *Ginkgo* and *Cistanche* combination in humans. Further, the examples above illustrate a mechanism of action for memory improvement for *Cistanche*.

A surprising and profound discovery was that *Ginkgo* supports the action of *Cistanche* in a synergistic way and that chronic treatment with *Cistanche* in vitro induced an increase in the global number of synapses and the number of synapses per neurite. This allows for spatial and temporal consolidation of neuronal signal which is known to play a key role in long term potentiation (LTP), the neural correlate of memory.

The results found were equal or better than the results from the positive control pharmaceutical compound (i.e., Donepezil; trade name Aricept) which is widely marketed for enhancement of cognition as an acetylcholinesterase (AChE or acetylhydrolase) inhibitor.

Neuronal Data Gathering and Analysis

Multichannel recording delivered single neuron spike data and spike identification and separation were accomplished with a template-matching algorithm in real time, to allow the extracellular recording of action potentials from 256 neurons simultaneously. The action potentials or "spikes" were recorded in spike trains and clustered in bursts, which can be quantitatively described via direct spike train analysis. High content analysis of the network activity patterns provides a multi-parametric description characterizing the activity in four categories: GA, BS, SY and OS. From the spike trains generated by this analysis, a total of 200 activity-describing spike train parameters were determined for each of these four categories.

Predominate Findings Using these Methods—Acute Application to Cell Cultures

Both *Cistanche* and *Ginkgo* extracts applied acutely to neuronal cultures affects network activity, *Cistanche* more so than *Ginkgo* with *Cistanche* changing GA and BS but *Ginkgo* only changing BS mildly. Further, a similarity was observed between the actions of a pharmaceutical drug marketed for cognitive improvement (i.e., Donepezil) and *Cistanche* in terms of the direction of parameter shifts, but this parameter shifting was not seen after acute application of *Ginkgo*.

Activity enhancing effects were observed for mixtures of *Cistanche* and *Ginkgo* as follows: 10% and 25% *Ginkgo* (remainder *Cistanche*) made neurons more sensitive to the actions of *Cistanche* in that GA, strengthening of the BS and stronger SY was induced at a lower overall concentration. Further, at this dilution (10-25% *Ginkgo* and 90-75% *Cistanche*) network stimulation was potentiated with a higher effect size.

Predominate Findings Using these Methods—Chronic Application to Cell Cultures 24 days of *Cistanche* treatment of hippocampal cell cultures in vitro enhanced spontaneous network activity, similar to that seen with chronic application of Donepezil, except that *Cistanche* effects were more pronounced than those of the pharmaceutical. Both Donepezil and *Cistanche* Induced an increase in global synapse numbers, but only *Cistanche* increased the number of synapses per neurite By using MEA neurochips to capture the neuronal activation patterns of the *Cistanche* and *Ginkgo* extracts on hippocampal cell cultures, synergistic activity has been shown when the *Cistanche* extract is diluted to 75-90% with 25-10% of *Ginkgo* extract. It has also been shown that chronic treatment of *Cistanche* can induce neuronal morphology changes that are indicative of improved synaptic connectivity to support long term potentiation and memory.

Ratios of *Ginkgo* and *Cistanche* have been identified that produce synergistic effects on neuronal activity patterns, including making neurons more sensitive to the actions of *Cistanche*; GA, strengthening of the BS and stronger SY between the firing of individual neurons. Further, at various dilutions, the combination of *Cistanche* and *Ginkgo* potentiated network stimulation with a higher effect size. In general a high level of *Ginkgo* (>50%) in combination with *Cistanche* will reduce the synergistic effect of the combination.

Moreover, the examples of this disclosure show that *Cistanche* can work alongside the natural neuronal strengthening effects of endogenous NGF. NGF is known to augment neuronal survival and to modify synaptic efficacy and neuronal plasticity. Staying mentally active, pursuing activities that bring mental satisfaction, and staying active through exercise, are positive behaviors for mental health. Each of these behaviors also increases endogenous production of NGFs in the brain. Thus, the combination of such behaviors and the compositions of this disclosure make a natural pairing with one another as complementary ways to strengthen and protect the longevity and robustness of cognitive abilities as a subject ages.

The terms "comprising" or "comprise" are used herein in their broadest sense to mean and encompass the notions of "including", "include", "consist(ing) essentially of", and "consist(ing) of". The use of "for example", "e.g.", "such as", and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-10, ±0-5, or ±0-2.5, % of the numerical values. Further, The term "about" applies to both numerical values when associated with a range of values. Moreover, the term "about" may apply to numerical values even when not explicitly stated.

Generally, as used herein a hyphen "-" or dash "—" in a range of values is "to" or "through"; a ">" is "above" or "greater-than"; a "≥" is "at least" or "greater-than or equal to"; a "<" is "below" or "less-than"; and a "≤" is "at most" or "less-than or equal to". On an individual basis, each of the aforementioned applications for patent, patents, and/or patent application publications, is expressly incorporated herein by reference in its entirety in one or more non-limiting embodiments.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

What is claimed is:

1. A method for treating a human with memory loss, said method consisting essentially of administering to the human with memory loss a therapeutically effective amount of a mixture of a *Cistanche tubulosa* extract and a *Ginkgo biloba* extract in a weight ratio of 2.6:1 to 20:1, respectively to effectively treat the human with memory loss.

2. The method as set forth in claim 1, wherein the weight ratio is 3:1 to 9:1, respectively.

3. The method as set forth in claim 2, wherein:
   i) the *Cistanche tubulosa* extract is present in an amount of from about 72-99 wt, based on 100 parts by weight of the mixture;
   ii) the *Ginkgo biloba* extract is present in an amount of from about 1-28 wt based on 100 parts by weight of the mixture; or
   iii) both i) and ii).

4. The method as set forth in claim 3, wherein the *Cistanche tubulosa* extract is a root extract.

5. The method as set forth in claim 3, wherein the *Ginkgo biloba* extract is a leaf extract.

6. The method as set forth in claim 1, wherein:
   i) the mixture is administered orally;
   ii) the mixture is in the form of a tablet; or
   iii) both i) and ii).

7. The method as set forth in claim 1, wherein:
   i) the *Cistanche tubulosa* extract is present in an amount of from about 72-99 wt based on 100 parts by weight of the mixture;
   ii) the *Ginkgo biloba* extract is present in an amount of from about 1-28 wt. % based on 100 parts by weight of the mixture; or
   iii) both i) and ii).

8. The method as set forth in claim 1, wherein the therapeutically effective amount provides at least about 250 mg of the *Cistanche tubulosa* extract to the human with memory loss.

9. The method as set forth in claim 1, wherein the composition mixture is administered to the human with memory loss on a periodic basis.

* * * * *

UNITED STATES PATENT AND TRADEMARK OFFICE
CERTIFICATE OF CORRECTION

PATENT NO.         : 9,737,582 B2
APPLICATION NO.    : 14/707132
DATED              : August 22, 2017
INVENTOR(S)        : Salter Venzon et al.

Page 1 of 1

It is certified that error appears in the above-identified patent and that said Letters Patent is hereby corrected as shown below:

In the Claims

Column 19, Claim 3, Line 15:
"99 wt," should be -- 99 wt. % --

Column 19, Claim 3, Line 18:
"28 wt" should be -- 28 wt. % --

Column 20, Claim 7, Line 9:
"99 wt" should be -- 99 wt. % --

Column 20, Claim 9, Lines 19 and 20:
"wherein the composition mixture" should be -- wherein the mixture --

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*